US010360675B2

(12) United States Patent
Reicher et al.

(10) Patent No.: US 10,360,675 B2
(45) Date of Patent: Jul. 23, 2019

(54) METHODS AND SYSTEMS FOR AUTOMATICALLY ANALYZING CLINICAL IMAGES USING RULES AND IMAGE ANALYTICS

(71) Applicant: INTERNATIONAL BUSINESS MACHINES CORPORATION, Armonk, NY (US)

(72) Inventors: Murray A. Reicher, Rancho Santa Fe, CA (US); Jon T. DeVries, Cary, NC (US); Michael W. Ferro, Jr., Chicago, IL (US); Marwan Sati, Mississauga (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 157 days.

(21) Appl. No.: 15/179,506

(22) Filed: Jun. 10, 2016

(65) Prior Publication Data

US 2016/0364631 A1 Dec. 15, 2016

Related U.S. Application Data

(60) Provisional application No. 62/174,946, filed on Jun. 12, 2015, provisional application No. 62/174,953, (Continued)

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0033* (2013.01); *A61B 5/7267* (2013.01); (Continued)

(58) Field of Classification Search
CPC .............. G06K 9/6256; G06K 9/6269; G06K 2209/051; G06K 9/6227; G06K 9/6232; (Continued)

(56) References Cited

U.S. PATENT DOCUMENTS 6,090,044 A 7/2000 Bishop et al.
6,574,304 B1 6/2003 Hsieh et al.
(Continued)

OTHER PUBLICATIONS

Chen et al., "An Automatic Diagnostic System for CT Liver Image Classification", IEEE Transactions on Biomedical Engineering, Jun. 6, 1998, pp. 783-794, vol. 45, No. 6.
(Continued)

*Primary Examiner* — Tom Y Lu
(74) *Attorney, Agent, or Firm* — Michael Best & Friedrich LLP

(57) ABSTRACT

Methods and systems for automatically analyzing clinical images using rules and image analytics. One system includes a server including an electronic processor and an interface for communicating with at least one data source. The electronic processor is configured to receive training information from the at least one data source over the interface. The training information includes a plurality of images and graphical reporting associated with each of the plurality of images. The electronic processor is also configured to perform machine learning to develop a model using the training information and receive an image for analysis. The electronic processor is also configured to determine a set of rules for the image and automatically process the image using the model and the set of rules to generate a diagnosis for the image.

17 Claims, 21 Drawing Sheets

US 10,360,675 B2
Page 2

Related U.S. Application Data filed on Jun. 12, 2015, provisional application No. 62/174,956, filed on Jun. 12, 2015, provisional application No. 62/174,962, filed on Jun. 12, 2015, provisional application No. 62/174,978, filed on Jun. 12, 2015.

(51) Int. Cl.

| | | |
|---|---|---|
| *G06F 19/00* | (2018.01) | |
| *G16H 50/50* | (2018.01) | |
| *G16H 15/00* | (2018.01) | |
| *G16H 50/20* | (2018.01) | |
| *G06N 20/00* | (2019.01) | |
| *A61B 5/00* | (2006.01) | |
| *G06F 3/0488* | (2013.01) | |
| *G06K 9/62* | (2006.01) | |
| *A61B 34/10* | (2016.01) | |
| *G06F 3/0482* | (2013.01) | |
| *A61B 10/02* | (2006.01) | |
| *G06T 11/00* | (2006.01) | |
| *G06F 17/24* | (2006.01) | |
| *G06F 17/27* | (2006.01) | |
| *G06K 9/66* | (2006.01) | |
| *G16H 30/20* | (2018.01) | |
| *G16H 10/20* | (2018.01) | |
| *A61B 90/00* | (2016.01) | |
| *A61B 5/01* | (2006.01) | |
| *A61B 5/0402* | (2006.01) | |
| *A61B 5/055* | (2006.01) | |

(52) U.S. Cl.
CPC .............. *A61B 10/02* (2013.01); *A61B 34/10* (2016.02); *G06F 3/0482* (2013.01); *G06F 3/0488* (2013.01); *G06F 17/241* (2013.01); *G06F 17/2705* (2013.01); *G06F 19/00* (2013.01); *G06F 19/321* (2013.01); *G06F 19/36* (2013.01); *G06K 9/627* (2013.01); *G06K 9/6227* (2013.01); *G06K 9/6232* (2013.01); *G06K 9/6256* (2013.01); *G06K 9/6262* (2013.01); *G06K 9/6269* (2013.01); *G06K 9/66* (2013.01); *G06N 20/00* (2019.01); *G06T 7/0014* (2013.01); *G06T 11/008* (2013.01); *G16H 10/20* (2018.01); *G16H 15/00* (2018.01); *G16H 30/20* (2018.01); *G16H 50/20* (2018.01); *G16H 50/50* (2018.01); *A61B 5/0077* (2013.01); *A61B 5/015* (2013.01); *A61B 5/0402* (2013.01); *A61B 5/055* (2013.01); *A61B 5/4312* (2013.01); *A61B 5/441* (2013.01); *A61B 2034/108* (2016.02); *A61B 2090/373* (2016.02); *A61B 2090/374* (2016.02); *A61B 2090/378* (2016.02); *A61B 2090/3762* (2016.02); *G06K 2209/051* (2013.01); *G06T 2200/24* (2013.01); *G06T 2207/10088* (2013.01); *G06T 2207/20081* (2013.01); *G06T 2207/30004* (2013.01); *G06T 2207/30008* (2013.01); *G06T 2207/30016* (2013.01); *G06T 2207/30052* (2013.01); *G06T 2207/30061* (2013.01); *G06T 2207/30068* (2013.01); *G06T 2207/30088* (2013.01)

(58) Field of Classification Search
CPC ........ G06K 9/6262; G06K 9/627; G06K 9/66; G06N 99/005; A61B 10/02; A61B 2034/108; A61B 2090/373; A61B 2090/374; A61B 2090/3762; A61B 2090/378; A61B 34/10; A61B 5/0033

See application file for complete search history.

(56) References Cited

U.S. PATENT DOCUMENTS

| | | | |
|---|---|---|---|
| 6,687,329 B1 | 2/2004 | Hsieh et al. | |
| 6,819,790 B2 | 11/2004 | Suzuki et al. | |
| 6,836,558 B2 | 12/2004 | Doi et al. | |
| 7,130,457 B2 | 10/2006 | Kaufman et al. | |
| 7,428,323 B2 | 9/2008 | Hillman | |
| 7,529,394 B2 * | 5/2009 | Krishnan | G06F 19/321 |
| | | | 128/922 |
| 7,640,051 B2 * | 12/2009 | Krishnan | G06F 19/321 |
| | | | 128/920 |
| 7,672,491 B2 | 3/2010 | Krishnan et al. | |
| 7,761,345 B1 | 7/2010 | Martin et al. | |
| 7,788,040 B2 * | 8/2010 | Haskell | G06Q 50/24 |
| | | | 435/6.11 |
| 7,949,167 B2 | 5/2011 | Krishnan et al. | |
| 8,021,045 B2 | 9/2011 | Foos et al. | |
| 8,199,985 B2 | 6/2012 | Jakobsson et al. | |
| 8,345,940 B2 | 1/2013 | Mattiuzzi et al. | |
| 8,478,698 B1 | 7/2013 | Mah | |
| 8,583,450 B2 | 11/2013 | Baker et al. | |
| 8,687,867 B1 | 4/2014 | Collins et al. | |
| 8,727,989 B2 | 5/2014 | Baba | |
| 8,879,813 B1 | 11/2014 | Solanki et al. | |
| 9,089,303 B2 | 7/2015 | Chen et al. | |
| 9,092,727 B1 | 7/2015 | Reicher | |
| 2004/0147840 A1 | 7/2004 | Duggirala et al. | |
| 2005/0010098 A1 | 1/2005 | Frigstad et al. | |
| 2005/0010445 A1 | 1/2005 | Krishnan et al. | |
| 2005/0021375 A1 | 1/2005 | Shimizu et al. | |
| 2005/0049497 A1 | 3/2005 | Krishnan et al. | |
| 2005/0113960 A1 | 5/2005 | Karau et al. | |
| 2005/0231416 A1 | 10/2005 | Rowe et al. | |
| 2005/0251013 A1 | 11/2005 | Krishnan et al. | |
| 2005/0255434 A1 | 11/2005 | Lok et al. | |
| 2006/0110018 A1 | 5/2006 | Chen et al. | |
| 2006/0159325 A1 | 7/2006 | Zeineh et al. | |
| 2006/0228015 A1 | 10/2006 | Brockway et al. | |
| 2006/0274928 A1 | 12/2006 | Collins et al. | |
| 2007/0036402 A1 | 2/2007 | Cahill et al. | |
| 2007/0078679 A1 | 4/2007 | Rose | |
| 2007/0118055 A1 | 5/2007 | McCombs | |
| 2007/0118399 A1 | 5/2007 | Avinash et al. | |
| 2007/0272747 A1 | 11/2007 | Woods et al. | |
| 2008/0046286 A1 | 2/2008 | Halsted | |
| 2008/0226147 A1 | 9/2008 | Hargrove et al. | |
| 2009/0080731 A1 | 3/2009 | Krishnapuram et al. | |
| 2009/0092300 A1 | 4/2009 | Jerebko et al. | |
| 2009/0326989 A1 | 12/2009 | Crucs | |
| 2010/0042422 A1 | 2/2010 | Summers | |
| 2010/0121178 A1 | 5/2010 | Krishnan et al. | |
| 2010/0312734 A1 | 12/2010 | Widrow | |
| 2011/0123079 A1 | 5/2011 | Gustafson | |
| 2011/0301447 A1 | 12/2011 | Park et al. | |
| 2012/0054652 A1 | 3/2012 | Kawagishi et al. | |
| 2012/0088981 A1 | 4/2012 | Liu et al. | |
| 2012/0172700 A1 * | 7/2012 | Krishnan | A61B 6/032 |
| | | | 600/407 |
| 2012/0189176 A1 | 7/2012 | Giger et al. | |
| 2012/0237109 A1 | 9/2012 | Rajpoot et al. | |
| 2012/0283574 A1 | 11/2012 | Park et al. | |
| 2012/0310399 A1 | 12/2012 | Metzger | |
| 2012/0328178 A1 | 12/2012 | Remiszewski et al. | |
| 2013/0090554 A1 | 4/2013 | Zvuloni et al. | |
| 2013/0149682 A1 | 6/2013 | Raab | |
| 2013/0204115 A1 | 8/2013 | Dam et al. | |
| 2013/0290225 A1 | 10/2013 | Kamath et al. | |
| 2013/0304751 A1 | 11/2013 | Yoshioka et al. | |
| 2013/0314434 A1 | 11/2013 | Shetterly et al. | |
| 2014/0010432 A1 | 1/2014 | Cohen-Solal et al. | |
| 2014/0121487 A1 | 5/2014 | Faybishenko et al. | |
| 2014/0155763 A1 | 6/2014 | Bruce | |

(56) References Cited

U.S. PATENT DOCUMENTS

| | | | |
|---|---|---|---|
| 2014/0161337 A1 | 6/2014 | Raykar et al. | |
| 2014/0185888 A1* | 7/2014 | Kelm | G06T 7/0014 |
| | | | 382/128 |
| 2014/0218397 A1 | 8/2014 | Rutman et al. | |
| 2014/0219526 A1 | 8/2014 | Linguraru et al. | |
| 2014/0244309 A1 | 8/2014 | Francois | |
| 2014/0257854 A1 | 9/2014 | Becker et al. | |
| 2014/0279807 A1* | 9/2014 | Dimitrijevic | G06N 5/025 |
| | | | 706/47 |
| 2014/0313222 A1 | 10/2014 | Anderson et al. | |
| 2014/0314292 A1 | 10/2014 | Kamen et al. | |
| 2014/0375671 A1 | 12/2014 | Giger et al. | |
| 2015/0065803 A1 | 3/2015 | Douglas et al. | |
| 2015/0072371 A1 | 3/2015 | Marugame | |
| 2015/0103170 A1 | 4/2015 | Nelson et al. | |
| 2015/0205917 A1* | 7/2015 | Mabotuwana | G06F 19/321 |
| | | | 382/128 |
| 2015/0230876 A1 | 8/2015 | Roe et al. | |
| 2015/0287192 A1 | 10/2015 | Sasaki | |
| 2015/0302317 A1 | 10/2015 | Norouzi et al. | |
| 2015/0320365 A1 | 11/2015 | Schulze et al. | |
| 2015/0331995 A1 | 11/2015 | Zhao et al. | |
| 2015/0332111 A1 | 11/2015 | Kisilev et al. | |
| 2016/0005106 A1 | 1/2016 | Giraldez et al. | |
| 2016/0275138 A1 | 9/2016 | Rutenberg et al. | |
| 2016/0283489 A1 | 9/2016 | Uy | |
| 2016/0350919 A1 | 12/2016 | Steigauf et al. | |
| 2016/0364862 A1 | 12/2016 | Reicher et al. | |
| 2017/0091937 A1 | 3/2017 | Barnes et al. | |
| 2017/0262584 A1 | 9/2017 | Gallix et al. | |
| 2018/0144421 A1 | 5/2018 | Williams et al. | |

OTHER PUBLICATIONS

Goldbaum et al., "Automated Diagnosis and Image Understanding with Object Extraction, Object Classification, and Inferencing in Retinal Images", Department of Ophthalmology and Department of Engineering and Computer Science, 1996, 4 pages, University of California, La Jolla, CA, USA.
Jun. 10, 2016, U.S. Appl. No. 15/179,506, US2016/0364631.
Jun. 10, 2016, U.S. Appl. No. 15/179,409, US2016/0364862.
Jun. 10, 2016, U.S. Appl. No. 15/179,434, US2016/0364526.
Jun. 10, 2016, U.S. Appl. No. 15/179,452, US2016/0364527.
Jun. 10, 2016, U.S. Appl. No. 15/179,465, US2016/0364528.
Jun. 10, 2016, U.S. Appl. No. 15/179,501, US2016/0364630.
Jun. 10, 2016, U.S. Appl. No. 15/179,674, US2016/0364539.
Jun. 10, 2016, U.S. Appl. No. 15/179,681, US2016/0361025.
Jun. 10, 2016, U.S. Appl. No. 15/179,448, US2016/0364857.
Jun. 10, 2016, U.S. Appl. No. 15/179,457, US2016/0361121.
Office Action from the US Patent and Trademark Office for U.S. Appl. No. 15/179,501 dated Oct. 10, 2017 (14 pages).
Office Action from the US Patent and Trademark Office for U.S. Appl. No. 15/179,681 dated Oct. 16, 2017 (30 pages).
Piccolo et al., "Dermoscopic diagnosis by a trained clinician vs. a clinician with minimal dermoscopy training vs. computer-aided diagnosis of 341 pigmented skin lesions: a comparative study", Bristish Journal of Dermatology, (2002), vol. 147, pp. 481-486, Bristish Association of Dermatologists.
Binder et al., "Application of an artificial neural network in epiluminescene microscopy pattern analysis of pigmented skin lesions: a pilot study", Bristish Journal of Dermatology, (1994), vol. 130, pp. 460-465.
Carlson et al., "Pancreatic cystic neoplasms: the role and sensitivity of needle aspiration and biopsy", Abdom Imaging, (1998), vol. 23, pp. 387-393, American Roentgen Ray Society, Washington D.C.
Office Action from the US Patent and Trademark Office for U.S. Appl. No. 15/179,465 dated Oct. 13, 2017 (31 pages).
Office Action from the US Patent and Trademark Office for U.S. Appl. No. 15/179,674 dated Oct. 30, 2017 (30 pages).
Scott et al., "Telemedical Diagnosis of Retinopathy of Prematurity: Intraphysician Agreement between Ophthalmoscopic Examination and Image-Based Interpretation", Opthamology, (Jul. 2008), vol. 115, No. 7.
Office Action from the US Patent and Trademark Office for U.S. Appl. No. 15/179,448 dated Oct. 31, 2017 (14 pages).
Office Action from the US Patent and Trademark Office for U.S. Appl. No. 15/179,457 dated Nov. 17, 2017 (15 pages).
Final Office Action from the U.S. Patent and Trademark Office for U.S. Appl. No. 15/179,465 dated Feb. 28, 2018 (32 pages).
Final Office Action from the U.S. Patent and Trademark Office for U.S. Appl. No. 15/179,681 dated Feb. 28, 2018 (23 pages).
Final Office Action from the U.S. Patent and Trademark Office for U.S. Appl. No. 15/179,434 dated Oct. 11, 2018 (27 pages).
Non-Final Office Action from the U.S. Patent and Trademark Office for U.S. Appl. No. 15/179,452 dated Oct. 19, 2018 (17 pages).
Notice of Allowance from the U.S. Patent and Trademark Office for U.S. Appl. No. 15/179,681 dated Oct. 30, 2018 (14 pages).
Notice of Allowance from the U.S. Patent and Trademark Office for U.S. Appl. No. 15/179,674 dated Oct. 18, 2018 (8 pages).
Non-Final Office Action from the U.S. Patent and Trademark Office for U.S. Appl. No. 15/179,409 dated Dec. 13, 2018 (47 pages).
Notice of Allowance from the U.S. Patent and Trademark Office for U.S. Appl. No. 15/179,434 dated Dec. 28, 2018 (9 pages).
Non-Final Office Action from the U.S. Patent Office for U.S. Appl. No. 15/179,409 dated Jun. 15, 2018 (11 pages).
Non-Final Office Action from the U.S. Patent and Trademark Office for U.S. Appl. No. 15/179,434 dated Mar. 12, 2018 (12 pages).
Final Office Action from the U.S. Patent Office for U.S. Appl. No. 15/179,501 dated Apr. 9, 2018 (15 pages).
Final Office Action from the U.S. Patent Office for U.S. Appl. No. 15/179,448 dated May 2, 2018 (15 pages).
Final Office Action from the U.S. Patent Office for U.S. Appl. No. 15/179,457 dated Apr. 30, 2018 (15 pages).
Non-Final Office Action from the U.S. Patent and Trademark Office for U.S. Appl. No. 15/179,674 dated Jul. 11, 2018 (14 pages).
Non-Final Office Action from the U.S. Patent and Trademark Office for U.S. Appl. No. 15/179,681 dated Jul. 9, 2018 (29 pages).
Kim, N. et al., "An Engineering View on Megatrends in Radiology: Digitization to Quantitative Tools of Medicine", Korean Journal of Radiology, Mar.-Apr. 2013, vol. 14, No. 2, pp. 139-153.
Teng. C., "Managing DICOM Image Metadata with Desktop Operating Systems Native User Interface", 22nd IEEE International Symposium on Computer-Based Medical Systems, 2009, (5 pages).
Doi, K., "Computer-aided diagnosis in medical imaging: Historical review, current status and future potential", Computerized Medical Imaging and Graphics, vol. 31, 2007, pp. 198-211.
Notice of Allowance from the U.S. Patent and Trademark Office for U.S. Appl. No. 15/179,465 dated Jul. 25, 2018 (1 pages).
Corrected Notice of Allowability from the U.S. Patent and Trademark Office for U.S. Appl. No. 15/179,681 dated Jan. 17, 2019 (7 pages).
Notice of Allowance from the U.S. Patent and Trademark Office for U.S. Appl. No. 15/179,448 dated Jan. 23, 2019 (9 pages).
Notice of Allowance from the U.S. Patent and Trademark Office for U.S. Appl. No. 15/179,457 dated Dec. 14, 2018 (8 pages).
Notice of Allowance from the U.S. Patent and Trademark Office for U.S. Appl. No. 15/179,501 dated Feb. 8, 2019 (9 pages).
Corrected Notice of Allowability from the U.S. Patent and Trademark Office for U.S. Appl. No. 15/179,674 dated Jan. 17, 2019 (7 pages).
Supplemental Notice of Allowability from the U.S. Patent and Trademark Office for U.S. Appl. No. 15/179,457 dated Feb. 1, 2019 (8 pages).
Final Office Action from the U.S. Patent and Trademark Office for U.S. Appl. No. 15/179,452 dated Mar. 8, 2019 (13 pages).
Supplemental Notice of Allowability from the U.S. Patent and Trademark Office for U.S. Appl. No. 15/179,448 dated Feb. 27, 2019 (4 pages).
Non-Final Office Action from the U.S. Patent and Trademark Office for U.S. Appl. No. 15/840,744 dated Mar. 5, 2019 (16 pages).

(56) References Cited

OTHER PUBLICATIONS

Supplemental Notice of Allowability from the U.S. Patent and Trademark Office for U.S. Appl. No. 15/179,434 dated Feb. 1, 2019 (5 pages).
Supplemental Notice of Allowability from the U.S. Patent and Trademark Office for U.S. Appl. No. 15/179,501 dated Mar. 27, 2019 (15 pages).
Corrected Notice of Allowability from the U.S. Patent and Trademark Office for U.S. Appl. No. 15/179,674 dated Mar. 25, 2019 (11 pages).
Corrected Notice of Allowability from the U.S. Patent and Trademark Office for U.S. Appl. No. 15/179,681 dated Mar. 25, 2019 (11 pages).
Supplemental Notice of Allowability from the U.S. Patent and Trademark Office for U.S. Appl. No. 15/179,448 dated Mar. 13, 2019 (7 pages).
Supplemental Notice of Allowability from the U.S. Patent and Trademark Office for U.S. Appl. No. 15/179,448 dated Apr. 1, 2019 (7 pages).
Supplemental Notice of Allowability from the U.S. Patent and Trademark Office for U.S. Appl. No. 15/179,457 dated Apr. 1, 2019 (7 pages).

* cited by examiner

FIG. 20

| Patient Name | Patient ID | Date of Birth | Reading Physician | Modality | Study Date | Patho Result |
|---|---|---|---|---|---|---|
| ⊟ *Andrea Anders | | | | | | |
| *Andrea Anders | 2103 | 12/19/1974 12:00:00 | Jonathan Stevens | | 01/01/2010 12:00:00 | N |
| *Andrea Anders | 2103 | 12/19/1974 12:00:00 | Phil Hotte | | 06/01/2010 12:00:00 | Y |
| ⊟ Alana Mickalek | | | | | | |
| Alana Mickalek | 1894 | 02/25/1987 12:00:00 | Jonathan Stevens | | 02/01/2009 12:00:00 | Y |
| Alana Mickalek | 1894 | 02/25/1987 12:00:00 | Jonathan Stevens | | 02/01/2009 12:00:00 | Y |
| Alana Mickalek | 1894 | 02/25/1987 12:00:00 | Jonathan Stevens | | 07/01/2009 12:00:00 | Y |
| ⊟ Alejandra Cuddy | | | | | | |
| Alejandra Cuddy | 1943 | 03/08/1955 12:00:00 | Jonathan Stevens | | 04/01/2008 12:00:00 | Y |
| Alejandra Cuddy | 1943 | 03/08/1955 12:00:00 | Jonathan Stevens | | 05/01/2008 12:00:00 | Y |
| Alejandra Cuddy | 1943 | 03/08/1955 12:00:00 | Jonathan Stevens | | 07/01/2010 12:00:00 | Y |
| Alejandra Cuddy | 1943 | 03/08/1955 12:00:00 | Jonathan Stevens | | 09/01/2009 12:00:00 | Y |
| ⊟ Alejandra Linnell | | | | | | |
| Alejandra Linnell | 2016 | 04/17/1941 12:00:00 | Jonathan Stevens | | 11/01/2008 12:00:00 | Y |
| Alejandra Linnell | 2016 | 04/17/1941 12:00:00 | Jonathan Stevens | | 08/01/2009 12:00:00 | Y |
| ⊟ Alejandra Mabey | | | | | | |
| Alejandra Mabey | 1858 | 02/14/1974 12:00:00 | Jonathan Stevens | | 06/01/2009 12:00:00 | Y |

(Work In Progress)
MERGE CADstream Analytics

StudyList | Reports        &rpalan Log Out

Study List

⊞ Choose Columns ⊕ Add Pathology        ←← ←Page 1 of 43 →→        1 - 25 of 1065

Study Information

BIRADS Category

Launch in CADstream

| ID | BIRADS | Pathology | Follow-up |
|---|---|---|---|
| 0 | 1 | | 6 Months |

Pathology Report: 02/02/2009 12:00:00 AM

Procedure Performed: Not Specified

Was there Malignant Tumor(s) found?
NO

What findings does the report show?
The resulting text for the Pathology Report will be placed here for review Unassociate Report ☐ Flag for education
☐ Flag Assessment as Discordant:

2002
2030

METHODS AND SYSTEMS FOR AUTOMATICALLY ANALYZING CLINICAL IMAGES USING RULES AND IMAGE ANALYTICS

RELATED APPLICATIONS

This application claims priority to U.S. Provisional Application Nos. 62/174,978; 62/174,962; 62/174,956; 62/174,953; and 62/174,946 all filed Jun. 12, 2015, and the entire content of each priority application is incorporated by reference herein.

FIELD

Embodiments of the present invention relate to systems and methods for performing image analytics using machine learning.

BACKGROUND

The number of medical images obtained worldwide continues to rapidly grow due to enhancements in imaging technology, including magnetic resonance imaging ("MRI"), spiral computed tomography ("CT"), position emission tomography ("PT"), ultrasound, various forms of radiography, mammography, breast tomosynthesis, medical photography and mobile imaging applications. The number of images generated using these and other technologies surpass the capacity of expert physicians (e.g., radiologists) to individually analyze each image. For example, a CT scan of an abdomen that once included 100 or fewer images now commonly includes 1,000 to 3,000 images. A physician who reports 50 CTs, MRIs, or PT scans in a day may now be required to view and analyze approximately 100,000 medical images from the current exams in addition to relevant prior exams for comparison. Also, there is now more clinical data from more sources that must also be integrated with imaging information.

Rather than simply replicating and speeding existing human processes, computers may simultaneously process multiple tasks and draw upon multiple simultaneous information sources based on interactive rules. Therefore, unlike the human brain, which is largely a serial processor, multitasking computer system may simultaneously weigh many factors, and therefore complement or exceed human performance with regard to medical image interpretation.

The ever-growing need to increase the speed and accuracy of medical image review, including the integration and consideration of clinical and reference data, demands improvements to medical image and information management systems. Methods and technologies described herein are therefore necessary and welcome additions to the art.

SUMMARY

Embodiments of the present invention provide systems and methods for developing image analytics using machine learning. For example, some embodiments of the invention use graphical reporting to train a learning engine. Graphical reporting includes images combined with structured data that allows the learning engine to more rapidly "learn" image characteristics and associated diagnoses. The learning engine may be executed by a computer system and may be configured to obtain training information, including graphical reporting, from one or more data sources. The sources may be connected to the computer system over one or more network connections, such as the Internet or other public or private networks.

As the learning engine is progressively trained, the learning engine (i.e., the models developed by the learning engine) may be used to analyze medical images and associated data to provide diagnostic information. In some embodiments, the diagnostic information may include categorization of an image or exam (comprised of one or more images) into various categories, such as: (1) normal, (2) abnormal, and (3) indeterminate. The models developed by the learning engine may be used in various medical scenarios, including emergency rooms, urgent care centers, clinics, nursing care facilities, home care locations, rural areas, third-world countries, and any other environment where medical images are performed without the benefit of an immediately available professional specializing in medical imaging. The models may be used to supplement a professional, replace a professional, assist a professional, triage images or exams for a professional, aggregate/analyze a professional's performance, and combinations thereof. For example, the models may be used to identify images in an exam considered are normal and, therefore, do not require professional interpretation, exams considered abnormal, exams requiring emergent attention, image regions for a particular image type that are most likely to show abnormalities, and combinations thereof with probabilities influenced via simultaneous aggregation and consideration of clinical, demographic, and external data (e.g., local epidemics).

Accordingly, embodiments of the invention combine graphical reporting with clinical data and deep machine learning to automatically create models that simultaneously weigh many factors to automatically analyze clinical images. The models may be used to triage medical imaging exams or images within an exam to categorize and indicate those images or exams that do not require human review, those images that require added human attention, those images that require routing to experts, or those images that may be useful as a reference image (e.g., an image used for teaching, marketing, patient education, or public health) that should be routed to one or more repositories. The models may also be used to automatically identify the most critical images within an imaging exam, most critical regions of images, or both based on clinical indications and pre-test probabilities that are derived from demographic, clinical, and external data. The models may also be used to generate automated pre-test and post-test probability reports relative to relevant diagnostic questions or configurable specified questions (e.g., "Is there a tumor?," "Is there a fracture?," "Is there a tube malposition?," and the like). The models may also parse images and exams into categories, such as normal, abnormal, and indeterminate, and may automatically select and present best comparison images or exams or indicate the most relevant image regions for comparison. The models may make these selections based on an analysis of data including indications, demographics, risks, clinical data, epidemiological data, or a combination thereof. Similarly, in some embodiments, the models are used to automatically present the best image plane for volumetric images or a comparison of volumetric images or to automate comparing exams, images, and image regions to best detect changes over time (e.g., new emerging cancer, aneurysm, etc.) or draw inferences about the contents of a tissue or lesion (e.g., this mass is probably composed of fat, this mass is probably benign, etc.). Output from the models may be used to automatically notify users of relevant clinical events that may impact the interpretation of image changes (e.g., this lesion is smaller but there was a de-bulking surgery since the last exam so it is not clear whether the chemotherapy is working).

In some embodiments, the models may also be applied based on rules and other configurable settings linked to a user (e.g., a diagnosing physician), a facility, an organization, an exam type, a body part, a geographic location, a season, and the like. Embodiments may also provide standards-based interoperable reporting of results and image labeling performed by the models to facilitate a close-loop feedback mechanism from users (e.g., PACS users). Embodiments may also provide automated outcome analysis and performance metrics, which may be judged by models developed using the learning engine.

For example, one embodiment provides a system for automatically analyzing clinical images using rules and image analytics developed using graphical reporting associated with previously-analyzed clinical images. The system includes a server including an electronic processor and an interface for communicating with at least one data source. The electronic processor is configured to receive training information from the at least one data source over the interface. The training information includes a plurality of images and graphical reporting associated with each of the plurality of images. Each graphical reporting includes a graphical marker designating a portion of one of the plurality of images and diagnostic information associated with the portion of the one of the plurality of images. The electronic processor is also configured to perform machine learning to develop a model using the training information. The electronic processor is also configured to receive an image for analysis. The electronic processor is also configured to determine a set of rules for the image. The electronic processor is also configured to automatically process the image using the model and the set of rules to generate a diagnosis for the image.

Other aspects of the invention will become apparent by consideration of the detailed description and accompanying drawings.

BRIEF DESCRIPTION OF THE DRAWINGS

FIG. 20 illustrates a graphical user interface displaying a table linking imaging results with pathology results according to some embodiments.

Figure 1:
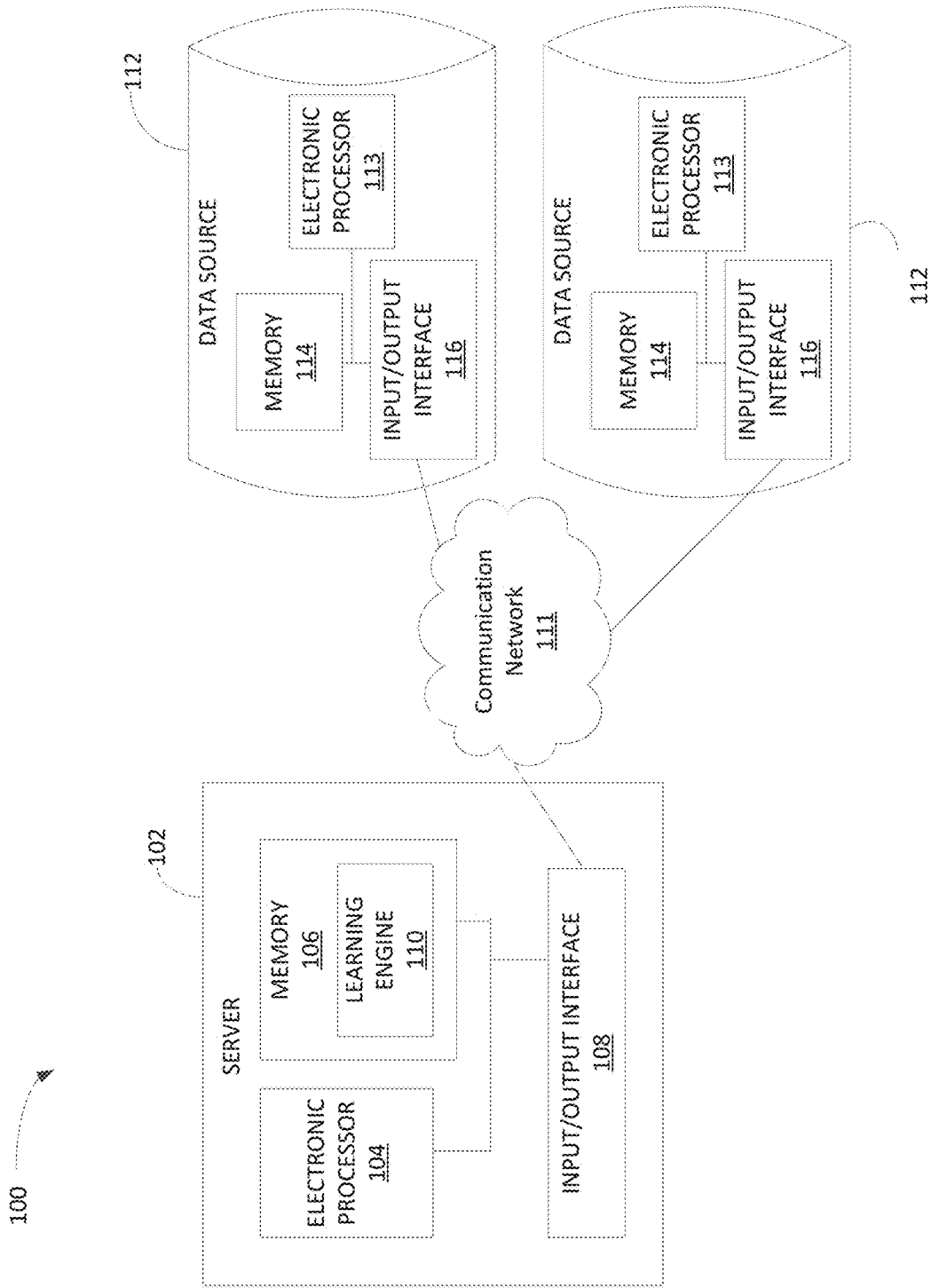
FIG. 1 illustrates a system for performing image analytics using machine learning according to some embodiments.

Other aspects of the invention will become apparent by consideration of the detailed description.

DETAILED DESCRIPTION

Before embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (e.g., stored on non-transitory computer-readable medium) executable by one or more processors. As such, it should be noted that a plurality of hardware and software based devices, as well as a plurality of different structural components, may be utilized to implement the invention. For example, "mobile device," "computing device," and "server" as described in the specification may include one or more electronic processors, one or more memory modules including non-transitory computer-readable medium, one or more input/output interfaces, and various connections (e.g., a system bus) connecting the components.

Machine learning generally refers to the ability of a computer program to learn without being explicitly programmed. In some embodiments, a computer program (e.g., a learning engine) is configured to construct a model (e.g., one or more algorithms) based on example inputs. Supervised learning involves presenting a computer program with example inputs and their desired (e.g., actual) outputs. The computer program is configured to learn a general rule (e.g., a model) that maps the inputs to the outputs. The computer program may be configured to perform machine learning using various types of methods and mechanisms. For example, the computer program may perform machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics.

Providing a learning engine with the proper example inputs and outputs may be a challenge, and analytics provided by a learning engine are generally only as good as the example inputs and outputs (hereinafter referred to as the "training information") provided. For example, when teaching a learning engine to analyze images by providing the learning engine with training information that includes previously-analyzed images, the learning engine needs to be able to identify what portions of an image are relevant for a particular diagnosis and what portions are irrelevant. The learning engine may benefit from knowing whether an image is associated with an abnormal diagnosis or a normal diagnosis and what clinical, demographic, or external data may be used to analyze the pre-test probability of a particular disease or finding. Historically, this information was not readily available for a particular medical image in ways that allowed a learning engine to effectively and efficiently learn from images.

Accordingly, embodiments of the invention provide methods and systems for providing training information to a learning engine to properly train the learning engine to automatically analyze medical images and provide diagnosis support. In particular, embodiments of the invention provide improvements to existing machine learning image processing technology by providing a learning engine with training information that informs the learning engine what portions of an image to analyze and information regarding findings (e.g., the contained normal/abnormal finding), diagnoses (e.g., a diagnosis or a differential diagnosis), confidence or probability rating of observations, and combinations thereof. Similarly, the training information provided to a learning engine may specify relevant images or portions of images from comparison imaging exams. The learning engine may use this information to detect diagnostic changes over time and to learn to compare images to derive diagnostic information. Thus, the learning engine may learn to detect an emerging breast cancer by comparing serial mammograms on the same patient or by comparing a left breast image to a corresponding right breast image taken from the same projection on the same day. Similarly, the learning engine may learn that a lesion yielding high signal on a T1-weighted MRI and low signal on a fast suppressed MRI taken at about the same time is likely composed of lipid. While learning, the learning engine may also simultaneously consider clinical and demographic data that comprise risk factors influencing the probability of a diagnosis or finding.

FIG. 1 illustrates a system 100 for performing machine learning according to some embodiments of the invention. The system 100 includes a server 102 that includes a plurality of electrical and electronic components that provide power, operational control, and protection of the components within the server 102. For example, as illustrated in FIG. 1, the server 102 may include an electronic processor 104 (e.g., a microprocessor, application-specific integrated circuit (ASIC), or another suitable electronic device), a memory 106 (e.g., a non-transitory, computer-readable storage medium), and an input/output interface 108. The electronic processor 104, the memory 106, and the input/output interface 108 communicate over one or more connections or buses. The server 102 illustrated in FIG. 1 represents one example of a server and embodiments described herein may include a server with additional, fewer, or different components than the server 102 illustrated in FIG. 1. Also, in some embodiments, the server 102 performs functionality in addition to the functionality described herein. Similarly, the functionality performed by the server 102 (i.e., through execution of instructions by the electronic processor 104) may be distributed among multiple servers. Accordingly, functionality described herein as being performed by the electronic processor 104 may be performed by one or more electronic processors included in the server 102, external to the server 102, or a combination thereof.

The memory 106 may include read-only memory ("ROM"), random access memory ("RAM") (e.g., dynamic RAM ("DRAM"), synchronous DRAM ("SDRAM"), and the like), electrically erasable programmable read-only memory ("EEPROM"), flash memory, a hard disk, a secure digital ("SD") card, other suitable memory devices, or a combination thereof. The electronic processor 104 executes computer-readable instructions ("software") stored in the memory 106. The software may include firmware, one or more applications, program data, filters, rules, one or more program modules, and other executable instructions. For example, the software may include instructions and associated data for performing the methods described herein. For example, as illustrated in FIG. 1, the memory 106 may store a learning engine 110 (i.e., software) for performing image analytics as described herein (e.g., processing training information to develop models). However, in other embodiments, the functionality described herein as being performed by the learning engine 110 may be performed through one or more software modules stored in the memory 106 or external memory.

The input/output interface 108 allows the server 102 to communicate with devices external to the server 102. For example, as illustrated in FIG. 1, the server 102 may communicate with one or more data sources 112 through the input/output interface 108. In particular, the input/output interface 108 may include a port for receiving a wired connection to an external device (e.g., a universal serial bus ("USB") cable and the like), a transceiver for establishing a wireless connection to an external device (e.g., over one or more communication networks 111, such as the Internet, a local area network ("LAN"), a wide area network ("WAN"), and the like), or a combination thereof.

In some embodiments, the server 102 also receives input from one or more peripheral devices, such as a keyboard, a pointing device (e.g., a mouse), buttons on a touch screen, a scroll ball, mechanical buttons, and the like through the input/output interface 108. Similarly, in some embodiments, the server 102 provides output to one or more peripheral devices, such as a display device (e.g., a liquid crystal display ("LCD"), a touch screen, and the like), a printer, a speaker, and the like through the input/output interface 108. In some embodiments, output may be provided within a graphical user interface ("GUI") (e.g., generated by the electronic processor 104 executing instructions and data stored in the memory 106 and presented on a touch screen or other display) that enables a user to interact with the server 102. In other embodiments, a user may interact with the server 102 through one or more intermediary devices, such as a personal computing device laptop, desktop, tablet, smart phone, smart watch or other wearable, smart television, and the like). For example, a user may configure functionality performed by the server 102 as described herein by providing data to an intermediary device that communicates with the server 102. In particular, a user may use a browser application executed by an intermediary device to access a web page that receives input from and provides output to the user for configuring the functionality performed by the server 102.

As illustrated in FIG. 1, the system 100 includes one or more data sources 112. Each data source 112 may include a plurality of electrical and electronic components that provide power, operational control, and protection of the components within the data source 112. In some embodiments, each data source 112 represents a server, a database, a personal computing device, or a combination thereof. For example, as illustrated in FIG. 1, each data source 112 may include an electronic processor 113 (e.g., a microprocessor, ASIC, or other suitable electronic device), a memory 114 (e.g., a non-transitory, computer-readable storage medium), and an input/output interface 116. The data sources 112 illustrated in FIG. 1 represents one example of data sources and embodiments described herein may include a data source with additional, fewer, or different components than the data sources 112 illustrated in FIG. 1. Also, in some embodiments, the server 102 communicates with more or fewer data sources 112 than illustrated in FIG. 1.

The input/output interface 116 allows the data source 112 to communicate with external devices, such as the server 102. For example, as illustrated in FIG. 1, the input/output interface 116 may include a transceiver for establishing a wireless connection to the server 102 or other devices through the communication network 111 described above. Alternatively or in addition, the input/output interface 116 may include a port for receiving a wired connection to the server 102 or other devices. Furthermore, in some embodiments, the data sources 112 also communicate with one or more peripheral devices through the input/output interface 116 for receiving input from a user, providing output to a user, or a combination thereof. In other embodiments, one or more of the data sources 112 may communicate with the server 102 through one or more intermediary devices. Also, in some embodiments, one or more of the data sources 112 may be included in the server 102.

The memory 114 of each data source 112 may store medical data, such as medical images (i.e., clinical images) and associated data (e.g., reports, metadata, and the like). For example, the data sources 112 may include a picture archiving and communication system ("PACS"), a radiology information system ("RIS"), an electronic medical record ("EMR"), a hospital information system ("HIS"), an image study ordering system, and the like. In some embodiments, as noted above, data stored in the data sources 112 or a portion thereof may be stored locally on the server 102 (e.g., in the memory 106).

Figure 2:
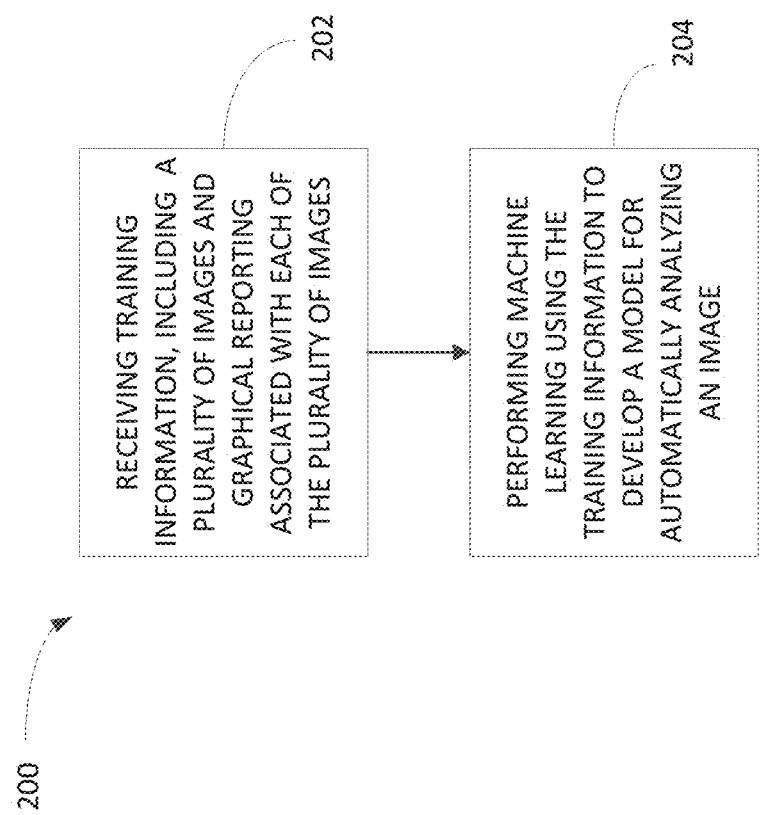
FIG. 2 is a flowchart of a method of performing image analytics using graphical reporting associated with clinical images according to some embodiment.

FIG. 2 is a flowchart illustrating a method 200 performed by the server 102 (i.e., the electronic processor 104 executing instructions, such as the learning engine 110) for automatically performing image analytics using graphical reporting associated with clinical images according to some embodiments. As described below, the learning engine 110 performs data analytics to discover meaningful patterns in images and builds models based on these discovered patterns, which can be used to automatically analyze images or other medical data. As illustrated in FIG. 2, the method 200 includes receiving, at the learning engine 110, training information (at block 202). The training information may take various forms, and in some embodiments, the training information includes data stored in the data sources 112. For example, the training information may include one or more images. The images may include radiographic images, magnetic resonance ("MR") images ("MRI"), ultrasonography ("US") images, endoscopy images, elastography images, tactile images, thermography, medical photography (e.g., photographs of skin conditions and other surface conditions, such as cleft palates, birth marks, moles, dislocations, and the like), computed tomography ("CT") images, electrocardiography ("ECG") data, position emission tomography ("PT") images, and the like. In some embodiments, the images provided to the learning engine 110 as training information may be pre-processed to improve training. For example, 2-D axial images may be preprocessed using a maximum intensity projection ("MIP") or multi-planar reconstruction ("MPR") algorithm. Also, in some embodiments, the learning engine 110 may be trained using multiple views of the same anatomy (e.g., axial, sagittal, coronal, or oblique planes). Also, the learning engine 110 may be trained using 3-D, 4-D, or even 5-D datasets, which are commonly collected as part of an imaging procedure but seldom used by diagnosing physicians.

In some embodiments, the training information also includes graphical reporting. Graphical reporting may refer to a method of reporting where an area of an image is graphically marked and the area is associated with diagnostic information (e.g., indicating that the identified area of the image illustrates a particular abnormality or a particular normality). The diagnostic information associated with the graphical marker may be structured or unstructured and may be in the form of text (generated manually by a diagnosing physician, automatically by a computer system, or a combination thereof), audio, video, images, and the like. The graphical marker may be created manually by a diagnosing physician, such as a radiologist, a cardiologist, a physician's assistant, a technologist, and the like or automatically by a computer system, such as a PACS. Similarly, the associated diagnostic information may be created manually by a diagnosing physician, such as a radiologist, a cardiologist, a physician's assistant, a technologist, and the like or automatically by a computer system, such as a PACS.

For example, a diagnosing physician reading a mammogram may mark one or more abnormalities on one or more of the images generated from the mammogram (a typical breast tomosynthesis exam contains approximately 300 or fewer images), such as by circling calcifications in one or more of the images. The diagnosing physician may also associate diagnostic information with each circled calcifications, such as the classification of "suspicious pleomorphic calcifications." The diagnosing physician may also generate a report that includes structured information describing image findings based on a particular lexicon, such as the American College of Radiology's ("ACR's") BI-RADS lexicon.

Figure 3:
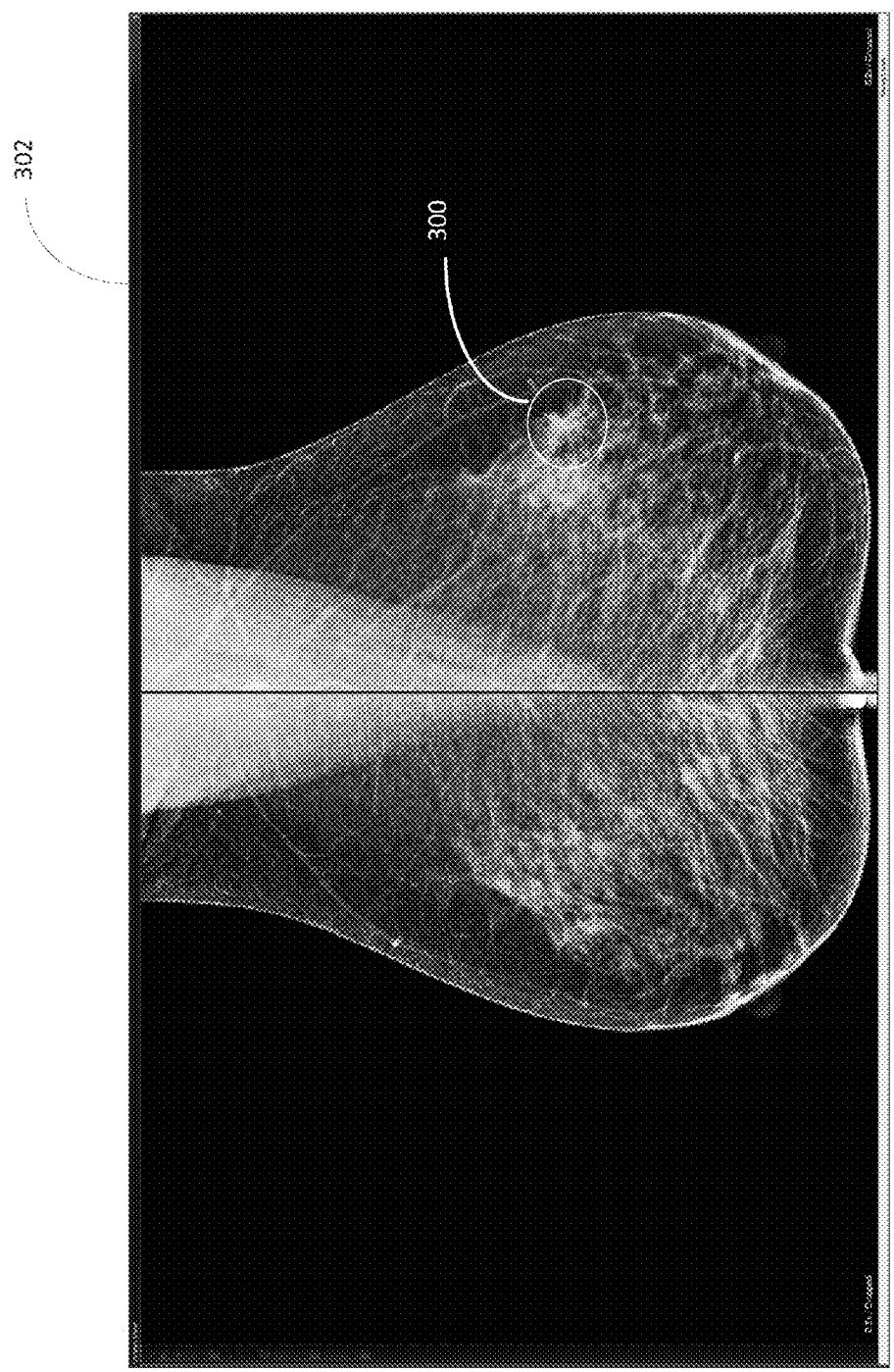
FIGS. 3 and 4 are images including a graphical marker according to some embodiments.
Figure 4:
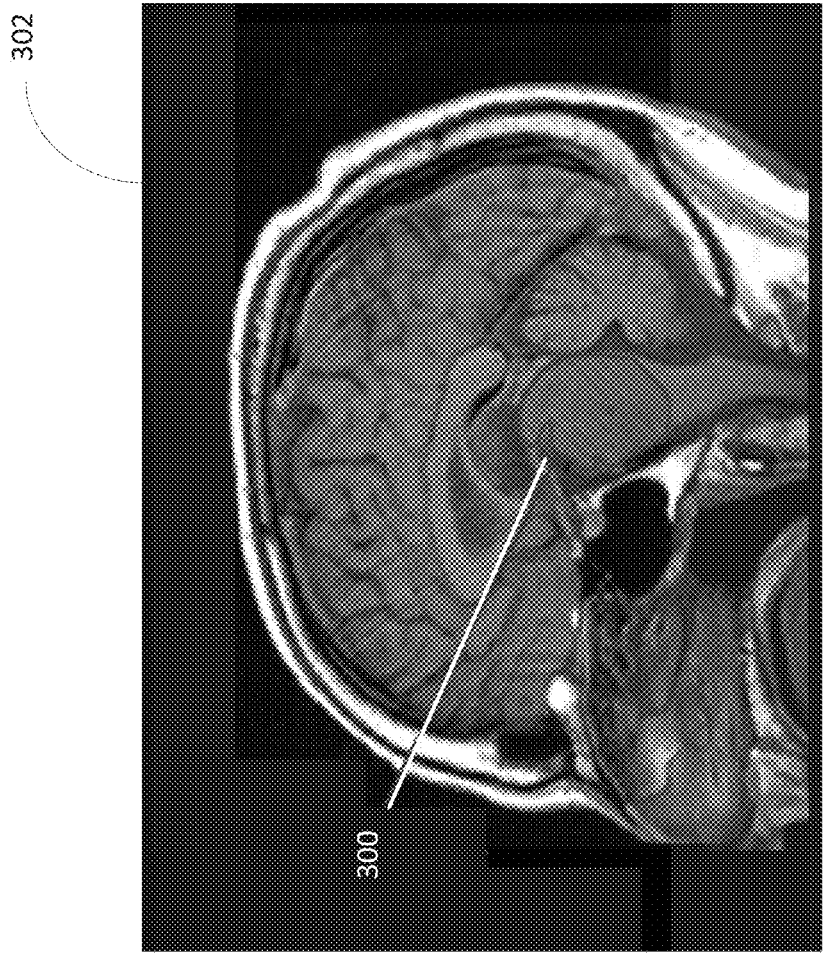

FIG. 3 illustrates an example graphical marker 300 added to an image 302. As illustrated in FIG. 3, the graphical marker 300 includes a circle surrounding an area of the image 302 of interest to the diagnosing physician. In addition to creating the graphical marker 300, a diagnosing physician (or a computer) provides diagnostic information associated with the area of the image 302 represented by the graphical marker 300. As noted above, the diagnostic information may be dictated by a diagnosing physician, selected by a diagnosing physician from a drop-down menu, generated by a PACS, or a combination thereof. Although the graphical marker 300 is illustrated in FIG. 3 as a circle, the graphical marker 300 may take different shapes and sizes, such as a point, an arrow, a line, a sphere, a rectangle, a cone, and the like and may be a one-dimensional marker, a two-dimensional marker, or a three-dimensional marker. For example, in some embodiments, the graphical marker 300 may follow a border or highlight an object represented in the image 302. For example, as illustrated in FIG. 4, the graphical marker 300 follows the border of the brainstem pons. In some embodiments, the shape or size of the graphical marker 300 may be manually set by the user performing the graphical reporting. In other embodiments, the shape or size of the graphical marker 300 may be automatically set by the graphical reporting software, such as based on the anatomy represented in the image 302, a portion of the image selected by the user, and the like. Also, an image may include one or more multiple graphical markers.

The images and the associated graphical reporting may be provided to the learning engine 110 to allow the learning engine 110 to rapidly learn to distinguish between a normal image and an abnormal image. In particular, by providing the learning engine 110 with the images and the associated graphical reporting, the learning engine 110 may associate a particular portion of an image with a particular diagnosis by knowing where to look within a particular image and how the marked area of the image was diagnosed. In other words, the graphical reporting provides the "where" (through the graphical marker) and the associated "what" (through the diagnostic information associated with the graphical marker), which allows the learning engine 110 to rapidly learn to analyze images. In particular, machine learning techniques that use images and corresponding structured reports to perform image analytics are missing an association between a diagnosis included in a structure report and areas of the image. For example, the structured report may indicate that the image is associated with a particular diagnosis (e.g., normal or abnormal) but does not specify an area of the image that led to the diagnosis.

As noted above, each graphical marker 300 may be associated with diagnostic information. In some embodiments, the diagnostic information is a classification or a delineation and classification over a spectrum (e.g., from benign to cancerous) that optionally includes an associated probability. For example, the diagnostic information may include a classification of a plurality of categories, such as a normal category, an abnormal category, or an indeterminate category. The classification may be based on the associated images, such as lesion morphology (e.g., a mass, a non-mass, or a focus lesion), lesion shape (e.g., round, oval, irregular, circumscribed, or spiculated), image properties of a tissue (e.g., homogeneous or heterogeneous distribution of image enhancement), or combinations thereof. In some cases, the classification may define dynamic imaging properties of a contrast agent (e.g., rate of wash-in and wash-out of contrast agent or the rate of contrast change on the borders of the lesion). In other cases, the classification may be based on the dynamic or static uptake of a radiopharmaceutical. The classification may also include the location of an area of interest with respect to an anatomical coordinate system, such as the upper-left quadrant of an organ. In some embodiments, the classification may specify an orientation of an area of interest, such as its alignment with anatomical structures (e.g., ducts). The classification may also specify a texture. In addition, in some embodiments, the classification indicates the results of blood tests, pathology results, genetic tests, or other clinical scores.

In addition to or as an alternative to a classification, the diagnostic information associated with a graphical marker may indicate a diagnosis, confidence level, a probability, a histology, a tumor grade, a stage, a differential diagnosis, a type of finding, an anatomical structure (e.g., organ(s) affected or other anatomical structures), an associated clinical syndrome, associated demographic information (such as age, gender, race/ethnicity, etc.), family history, problem lists, medications, allergies, immunizations, past therapies, and combinations thereof of that may be manually input or automatically pulled from a patient's electronic medical record. The diagnostic information may also include a measurement or a location within an image. The diagnostic information may also include morphological characteristics of an anomaly detected within an image.

In some embodiments, the training information also includes metadata associated with images. The metadata may include header information, such as a Digital Imaging and Communications in Medicine ("DICOM") header file, associated with an image included in the training information. The metadata may specify the "how" for the image, such as the imaging modality used, whether a contrast agent was used, the resolution or other settings for the imaging procedure, the imaging plane, the imaging technique, the field-of-view, slice thickness, date, and other imaging procedure or examination data. For example, a DICOM header file may specify what part of anatomy was being imaged. In some embodiments, when the metadata received by the learning engine 110 does not include anatomy information, the learning engine 110 may be configured to process the image and automatically identify the anatomy included in the image. Accordingly, in some embodiments, the learning engine 110 may be configured to generate metadata for received images.

The training information may also include imaging procedure or examination information associated with an image included in the training information. In some embodiments, the learning engine 110 may receive imaging procedure or examination data from an ordering system where the order for the image study originated. In some embodiments, the imaging procedure or examination information also includes information about who performed the imaging procedure (e.g., imaging clinic information, imaging technician information, and the like), or who analyzed the results of the imaging procedure (e.g., who generated the graphical reporting, such as an identifier of the diagnosing physician or an indication that the graphical reporting was automatically generated).

The training information may also include an imaging property of an image included in the training information. The imaging property may include an indication of whether a contrast agent or a radioactive isotope was used, a time after an agent or isotope was introduced, an orientation, and an image acquisition parameter (e.g., a MRI or CT radiation level).

The training information may also include patient information. In some embodiments, the patient information may be included in metadata associated with the images, such as the DICOM header file. In other embodiments, the patient information may be included separate from the images, such as in an HIS, EMR system, and the like. The patient information may specify the "who" for the image and may specify patient demographic information (e.g., age, gender, ethnicity, current residence, past residence, medical history, family medical history, biometrics, and the like). In some embodiments, the patient information may also include publicly-available patient information, such as information provided by the U.S. Center for Disease Control, World Health Organization, or other public health organizations, such as epidemics, trends, and the like. The patient information may also be obtained from non-medical sources, such as information available through social networking environments or other public information or data sources.

The training information may also include one or more reports (e.g., structured or unstructured) associated with the images. These associated reports may include an order, a DICOM structured radiology report, a pathology report, a test result (e.g., blood test results), and the like. For example, an MRI may be obtained after a potential cancerous lesion is detected on a medical image (e.g., an x-ray). The training information may include the image where the cancerous lesion was detected as well as the subsequent MRI findings. Similarly, a biopsy pathology result of the lesion may be included in the training information if available. As described below in more detail, the learning engine 110 may use the information about the lesion from both images and the pathology results when available to determine the accuracy of the image-based diagnosis. Accordingly, using this metadata allows the learning machine 110 to better perform multi-factorial diagnoses than a human diagnosing physician.

The reports may also include order records for the image study. For example, the order placed for a particular image study often provides information regarding what piece of anatomy was captured in the images and the reason for the image. If the reports are in text form, the learning engine 110 may use natural language processing or other document analysis technology to obtain metadata for a particular image. In some embodiments, the associated reports may include image studies for the patient associated with an image provided in the training information. For example, information relating to a patient's demographic, race, history, risk factors, family history, problem list, smoking history, allergies, lab test results, or prior imaging results may be used as training information for the learning engine 110.

The learning engine 110 may be configured to receive the training information from one or more data sources 112, including, for example, a PACS, a vendor neutral archive, a RIS, an EMR, a HIS, an image study ordering system, a computer assisted detection ("CAD") system, or a combination thereof. For example, in some embodiments, the learning engine 110 may receive the images and the associated graphical reporting from a PACS, RIS, and the like. The learning engine 110, however, may receive the other training information from devices different from the devices providing the images and associated graphical reporting. For example, when the learning engine 110 receives an image, the learning engine 110 may query one or more devices or systems, such as a HIS, an EMR, and the like, for imaging procedure or examination information or patient information. Also, in some embodiments, when performing the graphical reporting, the computer system may prompt the diagnosing physician for training information, such as a diagnosis, a measurement, an anatomy identification, patient information, imaging procedure or examination information, and the like.

In some embodiments, the systems generating the images for the learning engine 110 may be configured to collect training information and transmit the training information to the learning engine 110. In other embodiments, an intermediary device may be configured to receive an image from an image source (e.g., a PACS), access one or more sources to obtain additional training information, and generate a package of information for the learning engine 110. For example, in some embodiments, when an order is placed for an image study, a software application may be notified of the order, and the software application may store the order or information obtained from the order and wait for the corresponding images. For example, in some embodiments, an order often lists a destination for the resulting image study and associated report (e.g., the ordering physician, a specialist, a colleague, or the like). Therefore, when an order is (e.g., electronically) placed and submitted (e.g., manually or automatically), the order information may be automatically updated to include the learning engine 110 as a designated destination. Therefore, when an image report is created and associated with the image study (e.g., including a link to the associated image study), the report may be automatically transmitted to the learning engine 110 as training information. For example, in some embodiments the learning engine 110 may be configured to extract text from the image report and use a link included in the image report to access the associated image study.

Returning to the method 200 illustrated in FIG. 2, after the learning engine 110 receives the training information (at block 202), the learning engine 110 performs machine learning to develop a model using the received training information (at block 204). For example, in some embodiments, the learning engine 110 identifies an area of each image included in the training information and the associated diagnostic information based on the graphical reporting. For example, the graphical reporting may be represented as a data structure that includes coordinates of the graphical marker 300 and the associated diagnostic information (e.g., a categorization, a measurement, a probability, a risk factor, and the like). The data structure may also store an identifier of the image to which the data structure applies and also an identifier of the overall image study to which the data structure applies. Accordingly, the data records may be provided to the learning engine 110 separate from the associated images, and the learning engine 110 may be configured to apply the data structure to the image to identify the area of the image marked by the diagnosing physician and the corresponding diagnostic information. Alternatively or in addition, the graphical marker or indicator provided by a diagnosing physician may be superimposed on the image provided to the learning engine 110. Accordingly, the learning engine 110 may process the image to identify the marked region, such as by processing pixels to detect a region of pixels matching a particular shape, brightness, or color, or may employ meta-data to identify the coordinates of the marked region. In these configurations, images without the associated graphical marker or indicator may also be provided to the learning engine 110 (e.g., to allow the learning engine 110 to process the images without any interference that may be caused by the graphical marker placed on the images).

The learning engine 110 may also generate a data structure that associates an image with the graphical reporting (i.e., an area of the image and associated diagnostic information). The data structure may also include the additional training information received by the learning engine 110, such as the metadata, imaging procedure or examination information, patient information, or a combination thereof. The learning engine 110 may use some of the training information to develop a model for particular types of images or image studies. For example, when the DICOM header file indicates that an image is a CT spinal image, the learning engine 110 may group this training information with other training information for CT spinal images, which the learning engine 110 may use to develop a customized model associated with CT spinal images. Similarly, the learning engine 110 may be configured to develop different models for different types of images (e.g., ECG data versus CT images) regardless of the underlying anatomy. In addition, the learning engine 110 may use patient demographic information to group training information associated with abdomen scans for 20-year-old women separately from training information associated with abdomen scans for 60-year-old men. Also, in some embodiments, the learning engine 110 may develop models that consider external factors, such as geographic location, season, existing epidemics, or community immunization patterns.

Including graphical reporting in the training information may also enable the learning engine 110 to learn to inspect a particular portion of a comparison image. For example, a diagnosing physician may explicitly mark a proper comparison image and region as part of a graphical marker. Thus, the learning engine 110 may be taught not just to interpret a single image or exam but also how to best select comparison images and what portion of those images are to be used for comparison.

For example, the learning engine 110 may be configured to perform the machine learning to develop the model using the training information by evaluating a first portion designated by a first graphical marker within a first image included in the training information on a second image included in the training information, wherein the second image was acquired using a different imaging condition than the first image. For example, the second image may be a different image within the same exam as the first image, a different exam than the exam including the first image, an image acquired at a different time after injection of an agent or isotope than the first image, an image acquired using a different MRI acquisition parameter than the first image, an image acquired using a different radiation parameter than the first image, or a combination thereof.

As noted above, machine learning generally refers to the ability of a computer program to learn without being explicitly programmed and may be performed using various types of methods and mechanisms. For example, machine learning may be performed using decision tree learning, association rule learning, artificial neural networks, inductive logic programming, support vector machines, clustering, Bayesian networks, reinforcement learning, representation learning, similarity and metric learning, sparse dictionary learning, and genetic algorithms.

In some embodiments, the learning engine 110 assigns a weight to the training information or a portion thereof. For example, the learning engine 110 may be configured to obtain clinical results obtained after generation of an image included in the training information and perform a comparison of the clinical results and to the diagnostic information associated with the image (i.e., also included in the training information). The learning engine 110 may then assign a weight to the diagnostic information based on the comparison, wherein the learning engine 110 develops the model based on the weight. In some embodiments, the clinical results include at least one image, at least one laboratory result, or a combination thereof.

Similarly, in some embodiments, after developing a model using the training information, the learning engine 110 may update the model based on feedback designating a correctness of the training information or a portion thereof (e.g., diagnostic information included in the training information). For example, in some embodiments, the learning engine 110 updates a model based on clinical results (e.g., an image, a laboratory result, or the like) associated with one or more images included in the training information. In other embodiments, a user may manually indicate whether diagnostic information included in the training information was correct as compared to an additional (e.g., a later-established) diagnosis. Further details are provided below regarding uses of feedback.

When the learning engine 110 develops one or more models (i.e., when the learning engine 110 is considered trained), the models may be used to automatically analyze images. For example, FIG. 5 illustrates a method 500 performed by the server 102 (i.e., the electronic processor 104 executing instructions, such as the learning engine 110) for automatically analyzing clinical images using image analytics developed using graphical reporting associated with previously-analyzed clinical images according to some embodiments.

Figure 5:
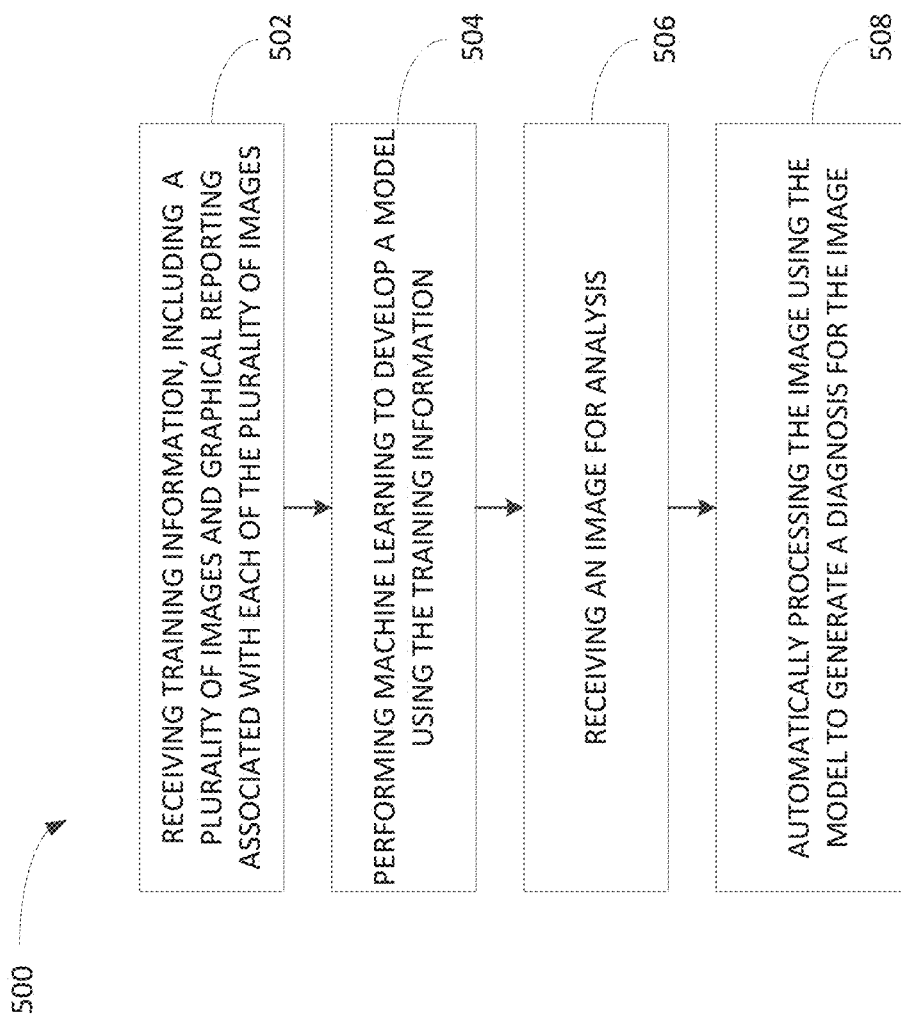
FIG. 5 is a flowchart of a method of automatically analyzing clinical images using image analytics developed using graphical reporting associated with previously-analyzed clinical images according to some embodiments.

As illustrated in FIG. 5, the method 500 includes receiving, with the learning engine 110, training information from at least one data source 112 over an interface (e.g., the input/output interface 108) (at block 502) and performing machine learning to develop a model using the training information (at block 504). As described above with respect to FIG. 2, the training information includes a plurality of images and graphical reporting associated with each of the plurality of images. As also described above, graphical reporting includes a graphical marker designating a portion of an image and diagnostic information associated with the marked portion of the image.

After the model is developed, the method 500 includes receiving, with the learning engine 110, an image for analysis (at block 506). The learning engine 110 may receive the image for analysis from one or more of the data sources 112. In other embodiments, the learning engine 110 may receive the image for analysis through a browser application (e.g., uploaded to a web page hosted by the server 102 or another device). In some embodiments, the learning engine 110 also receives supplemental data associated with the image for analysis, such as metadata associated with the image. The metadata may include order information, patient information (e.g., demographic information, historical information, family history information, and the like), modality information, procedure information, EMR information, laboratory information, public information (e.g., data from the Center of Disease Control or other public health organizations), and the like. The learning engine 110 may request this supplemental data from the data sources 112 or other devices, such as through the communication network 111. For example, in some embodiments, the learning engine 110 may request order information for the image, which the learning engine 110 uses to identity additional supplemental data that may be useful for analyzing the image (e.g., medical history information, patent demographic information, and the like). The learning engine 110 may use the supplemental data to determine what models should be used to process the image. For example, the learning engine 110 may process images associated with detecting breast cancer using different models than images associated with detecting fractures.

As illustrated in FIG. 5, the method 500 also includes automatically processing, with the learning engine 110, the received image using the model to generate a diagnosis (i.e., a result) for the image (at block 508). The learning engine 110 may output or provide a diagnosis in various forms. For example, in some embodiments, the learning engine 110 outputs a signal to a peripheral device, such as a display device (e.g., monitor, touchscreen, and the like), a printer, and the like, that includes the diagnosis. For example, the learning engine 110 may generate a graphical user interface that includes the diagnosis, wherein the graphical user interface is output to and displayed on a monitor, touchscreen, or other display device. The monitor may be included in peripheral device communicating with the server 102 or a computing device communicating with the server 102, such as a laptop computer, desktop computer, tablet computer, smart phone, smart watch or other wearable, smart television, and the like. Also, in some embodiments, the learning engine 110 may generate an electronic notification, such as an e-mail message, a Direct protocol message, or the like, that includes the diagnosis. The learning engine 110 may transmit the electronic notification to an email server, a HIS, a EMR, or another system. Also, in some embodiments, the learning engine 110 may store the diagnosis to memory (e.g., local to the device performing the image analysis or a separate device) for later retrieval.

In some embodiments, the learning engine 110 may incorporate the diagnosis into radiologist workflow, such that the diagnosis is presented on a radiologist's workstation. For example, the learning engine 110 may be configured as a vendor neutral system (i.e., the server 102 may interact with systems, such as RIS, HIS, PACS, and the like, provided by numerous different providers) that communicates with a reading workstation optimized to accept and use information from the server 102. For example, the workstation may be configured to present radiologists with annotated images generated by the learning engine 110 in a format that allows the radiologist to edit the images, including the annotations, within a viewer (e.g., through a medical image annotation tool). In some embodiments, edits made by the radiologist to the annotated images are fed back to the learning engine 110, which uses the edits to improve the developed models. Similarly, in some embodiments, the learning engine 110 may also be configured to generate a diagnosis that includes a measurement associated with the image and the measurements may be displayed when the images are displayed (e.g., as an overlay). For example, the learning engine 110 may be configured to determine the volume of a lesion, which may be displayed with an image. Also, in some embodiments, the learning engine 110 may be configured to automatically determine and display a reconstruction imaging plane that best shows a particular measurement, such as the maximum diameter of a volumetric lesion.

Similarly, the learning engine 110 may be configured to output the diagnosis in an interoperable manner (e.g., to a PACS or a reporting system) such that reports (e.g., structured DICOM reports) are pre-populated with the diagnosis. In some embodiments, a user may configure rules to designate what diagnoses generated by the learning engine 110 are mapped to particular data fields of one or more reports. This reporting process may leverage standards, such as the Annotation and Image Markup Standard, American College of Radiology ("ACR") Assist, or the Integrating the Healthcare Enterprise's ("IHE's") Management of Radiology Report Templates ("MRRT") Profile. In addition, the reporting process may be interoperable with existing or emerging industry standards for marking images, such as the Annotation and Image Markup standard. Interoperability may enable a wide variety of PACS users to provide close-loop feedback as described above, which expands the population feeding training information to the learning engine 110.

Diagnoses generated by the learning engine 110 and included in reports may be approved by a diagnosing physician and user-specific, role-specific, organization-specific, facility-specific, region-specific, modality-specific, or exam-specific rules may be used to control the approval process. For example, a PACS or similar reporting system may present a pre-processed report to a diagnosing physician and allow the diagnosing physician to edit or approve specific sections of the report or the report in its entirety (e.g., via an input action, such as selection of a button, checkbox, radio button, and the like and/or an electronic signature). As noted above, modifications made to the report may be returned to the learning engine 110 either automatically (e.g., by a rule) or manually on an ad hoc basis for continued refinement of the models.

The diagnosis may take many different forms, including for example, an indication of particular abnormality or anomaly (or the lack thereof) (e.g., cancer, fracture, blockage, bleeding, and the like), an indication of a disease, condition, or syndrome, a measurement or morphological characteristic, an indication of an anatomical structure, or a combination thereof. For example, in some embodiments, the diagnosis generated by the learning engine 110 may include a classification of an image into one of a plurality of categories, such as: (1) normal (or normal with regard to a particular characteristic, such as a fracture not being present), (2) abnormal (or abnormal with regard to a particular characteristic, such as a fracture being present), and (3) indeterminate. These classifications may be used in various medical situations. For example, a categorization generated by the learning engine 110 may be used to provide immediate diagnoses. In particular, a patient may take a picture of a skin lesion (e.g., using a software application on a mobile device, such as a smartphone or smart wearable), submit the image to the learning engine 110 for analysis (e.g., over the Internet), and receive an immediate diagnosis regarding whether the lesion is malignant melanoma (or a recommendation that the patient see a dermatologist or other specialist). Similarly, the learning engine 110 may automatically analyze emergency room radiographs and automatically identify images showing a specific abnormality (e.g., a fracture). The learning engine 110 may flag the identified images to ensure that a patient is not inappropriately sent home without proper treatment (e.g., sent home with an untreated fracture or untreated internal bleeding). Also, in some embodiments, the learning engine 110 may triage patients based on the analyzed images.

The learning engine 110 may also categorize images to flag images needing manual review. For example, the learning engine 110 may label images stored in a PACS system as "normal," "abnormal," or "indeterminate," and a diagnosing physician or other healthcare professional may use this information to triage images (e.g., prioritize images categorized as "abnormal" or "indeterminate"). For example, when an image study including a plurality of images is submitted to the learning engine 110 for analysis, the learning engine 101 may flag at least one of the plurality of images included in the image study for manual review based on the categorization of each image of the plurality of images. Similarly, the learning engine 110 may automatically identify images or exams that need to be sent to an external reading service. In addition, in some embodiments, the learning engine 110 automatically identifies images as reference images that may be stored in various repositories and used for research, teaching, marketing, patient education, public health, or other purposes.

In some embodiments, the learning engine 110 may also determine a probability for a diagnosis (e.g., a probability that the associated diagnosis is correct). The probabilities may be used similar to the categories described above (e.g., to triage images for review or to provide immediate diagnoses). In some embodiments, the learning engine 110 may also generate a basis for a probability (e.g., "The lesion has a smooth border; therefore, there is a low probability that the lesion is malignant."). In some situations, the learning engine 110 may generate multiple diagnoses and may associate a probability with each diagnosis that may be displayed to a user (e.g., ranked) to provide the user with possible diagnoses and their associated probabilities as a differential diagnosis.

In some embodiments, the learning engine 110 may use thresholds to categorize images as described above. For example, the learning engine 110 may identify a value for an image (e.g., a measurement, a probability, or the like) and may compare the determined value to one or more thresholds to identify what category the image belongs to. In some embodiments, users can configure (i.e., adjust) the thresholds. For example, a user may adjust a threshold to include more or fewer images within a particular category. As described below, these types of adjustments (e.g., preferences or rules) may be set at an individual level or a group level.

The learning engine 110 may also use the categories or associated thresholds to take particular automatic actions. For example, the learning engine 110 may determine a value for an image and compare the value to one or more thresholds. When the value satisfies a particular threshold (e.g., an accuracy threshold or a physical measurement or characteristics threshold, such as the length of size of a fracture), the learning engine 110 takes one or more automatic actions, such as discharging a patient, scheduling a procedure for the patient, placing an order for a procedure (e.g., an imaging procedure, a laboratory procedure, a treatment procedure, a surgical procedure, or a combination thereof), and the like. Similarly, the learning engine 110 may be configured to automatically provide recommendations based on determined categories or associated thresholds. For example, the learning engine 110 may generate a report that states when follow-ups are needed or recommended and what type of follow-up should be performed for a particular diagnosis (e.g., "Pre-test probability of a breast cancer in this patient is 1%. Based on image and clinical analytics, the post-test probability has increased to 1.8%. Consider 6 month follow-up mammogram."). The follow-ups may include an imaging procedure, a laboratory procedure, a treatment procedure, a surgical procedure, an office visit, or a combination thereof.

The learning engine 110 may also incorporate a diagnosis into one or more reports (e.g., structured reports, such as DICOM structured reports). The reports may include text, annotated images, flow charts, graphs, image overlays, image presentation states, or other forms. For example, as described above, a diagnosis determined by the learning engine 110 may be mapped to a particular data field of a structured report that is used to automatically pre-populate at least a portion of the structured report. As also described above, a diagnosing physician or other healthcare professional may review these resulting reports or portion thereof and make modifications as necessary. The learning engine 110 may use the modifications as a feedback loop that accelerates and improves machine learning. For example, the learning engine 110 may detect an abnormality in an image that a diagnosing physician disagrees with or vice versa, and the learning engine 110 may use this feedback to further refine the developed models.

Also, in some embodiments, the diagnosis includes an image annotation, such as a graphical marker as described above. For example, the learning engine 110 may automatically add one or more graphical markers to an image that specify relevant areas of an image for manual review. In some embodiments, these marked images may be included in or associated with a corresponding report, such as a DICOM structured report.

In some embodiments, the diagnosis generated by the learning engine 110 includes both an annotated image and corresponding diagnostic information. For example, the learning engine 110 may use the models to automatically select relevant exams or images for comparison, including determining advantageous comparison time frames. The learning engine 110 may select comparison images using a patient's medical history information, such as the timing of prior surgical or medical therapy. For example, by simultaneously weighing many factors, the learning engine 110 may automatically mark a lesion on an image and generate a corresponding report or notification that indicates influences on the marked lesions, such as "Lesion has decreased in size since date X; likely reasons include surgical debulking on date Y, and chemotherapy on date Z." Accordingly, in some embodiments, the learning engine 110 determines an amount of change between two or more images and notifies users of a prior procedure or treatment potentially impacting anatomy represented in an image. The notifications may include a graphical indication or a textual indication. For example, as described above, the learning engine 110 may generate a textual description of prior procedures or treatment potentially impacting imaged anatomy. Alternatively or in addition, the learning engine 110 may add a graphical mark (e.g., an icon) to an image that represents a prior procedure or treatment (e.g., generally or a specific type of prior procedure or treatment). When a graphical indication is used, a user may select (e.g., click on) the graphical indication to view the relevant medical history information. Similarly, in some embodiments, the learning engine 110 may generate a data structure that tracks changes in a detected anomaly over a sequence of images. The learning engine 110 may cross-reference changes stored in the data structure with at least one medical procedure or treatment performed on a patient to allow a user to identify the results (or lack thereof) of the procedure or treatment represented within images. For example, in some embodiments, the learning engine 110 may be configured to automatically register and compare serial exams to make comparisons and report differences. In particular, the learning engine 110 may be configured to automatically graph or otherwise access changes in a lesion or lesions over a period of time and issue a report using a standardized methodology, such as a RECIST 1.1 table.

Similarly, the learning engine 110 may use medical history information of a patient, such as clinical notes to automatically determine a portion of an image of clinical concern. For example, when a patient arrives at an emergency room and indicates that he struck his thumb with a hammer, this information (i.e., a patient complaint, an anatomical structure associated with the complaint, and the like) may be stored as clinical notes (e.g., in a patient's EMR). The learning engine 110 may use these clinical notes when processing x-ray images of the patient's hand to determine one or more portions of the image that may be of clinical concern. In particular, the learning engine 110 may determine a portion of the x-ray image region representing the patient's thumb, or, in particular, a tip of the patient's thumb. The learning engine 110 may indicate the determined portion using a textual indication or a graphical indication that is displayed with the x-ray image or on the x-ray image. Accordingly, when a diagnosing physician reviews the x-ray image, the indication directs the diagnosing physician's attention to the relevant portion of the x-ray image (i.e., the thumb or the tip of the thumb). Thus, the diagnosing physician is better able to diagnose the x-ray image. In some embodiments, the learning engine 110 may automatically learn these correlations based on training information that includes marked areas of images and corresponding clinical notes. Furthermore, as described above, in some embodiments, the learning engine 110 learns to identify anatomical structures within an image using the training information. Accordingly, the learning engine 110 may identify an anatomical structure based on the clinical notes associated with an image submitted for analysis and then automatically identify and mark the corresponding anatomical structure in the associated image.

In some applications, the models developed by the learning engine 110 may be used when a diagnosing physician is not available, such as during emergency, disaster, and military situations or in rural areas where diagnosing physicians are not readily available. Similarly, the models may be used to automatically identify what image studies should be sent to an expert reading service. Also, in some situations, the models may be used in place of a diagnosing physician, such as in reading ECG data, where the models may provide a high level of accuracy akin to that of a diagnosing physician. Also, as described in more detail below, the models may be "tuned" to a particular user (e.g., a diagnosing physician or other healthcare provider), facility, organization, nation, geographic region, or season of the year. For example, the learning engine 110 may generate a chest radiograph report that includes a statement such as, "Pulmonary hazy opacity. Consider flu season and locally reported SARS epidemic."

Accordingly, the models developed using the training information described above may be used for many purposes, including, for example and without limitation, automatically identifying lesions as suspicious for melanoma based on skin images (e.g., photographs), automatically reading ECG data to a greater accuracy than a human diagnosing physician or eliminating the need for human review of some ECG data, eliminating the need for physicians to view mammogram exams or images, driving physicians to more carefully inspect some images of a CT exam preferentially over others, identifying patients with intracranial hemorrhages on a CT scan performed in emergency room settings or other settings, performing automatic review of images obtained via endoscopy, colonoscopy, or CT colonography, automatically detecting nodules on CT scans that are suspicious for lung cancer as part of a screening program, automatically detecting compression fractures in lumbar imaging exams, and automatically detecting spinal stenosis or abnormal discs in lumbar imaging exams.

In some embodiments, the learning engine 110 may also be configured to determine when additional information is needed or beneficial to generate a diagnosis. For example, the learning engine 110 may have certain diagnoses (e.g., differential diagnoses) that the learning engine 110 knows can be refined with certain additional information, such as an additional image, patient demographic information, medical history information, a laboratory result, and the like. Accordingly, when the learning engine 110 receives an image for analysis, the learning engine 110 may determine whether additional information is needed (e.g., using the models). When the additional information is needed, the learning engine 110 may ask a user whether he or she wants to provide the additional information to refine the diagnosis (e.g., by displaying an icon that the user can select or providing another prompt). In some embodiments, the learning engine 110 may also inform the user what types of additional information (e.g., how many questions may be asked) may be requested and what impact the additional information may have (e.g., eliminate one or ten potential diagnoses). Alternatively or in addition, a user may configure the learning engine 110 to automatically request the additional information. When the learning engine 110 receives the requested additional information, the learning engine 110 generates a diagnosis as described above using the models and the additional information. For example, when the learning engine 110 generates an initial diagnosis that indicates a rare disease commonly only reported in African countries, the learning engine 110 may be configured to request additional information regarding whether the patient recently traveled outside of the U.S. or interacted with others who received traveled outside of the U.S. to determine the probability of the initial diagnosis. Similarly, when the learning engine 110 detects air within an abdomen represented in an image, the learning engine 110 may ask a user (e.g., a nurse) whether the patient associated with the image has undergone any surgical or other procedures in the past (e.g., the past ten days) that would explain the detection of air.

In some embodiments, the learning engine 110 prompts one or more users (e.g., the patient, one or more users associated with the care of a patient, or a combination thereof) for the additional information, automatically accesses the additional information from at least one electronic data repository (e.g., a HIS, an EMR, or the like), or performs a combination thereof. The learning engine 110 may prompt a user for the additional information within an image review application. Alternatively or in addition, the learning engine may prompt a user for the additional information by transmitting an electronic message to the user, such as a page, an e-mail message, a Direct protocol message, a text message, a voicemail message, or a combination thereof. In some embodiments, a user may define one or more preferences for these prompts. The preferences may specify when a user is prompted for additional information, how the user is prompted for the additional information (e.g., page followed by email or only email once a day), or a combination thereof. For example, the preferences may include a threshold associated with an initial diagnosis, and the learning engine 110 may prompt the user for additional information only when a probability associated with an initial diagnosis (i.e., a diagnosis determined without the additional information) is less than the threshold. As another example, the preferences may include a threshold associated with an updated or refined diagnosis. For example, the threshold may specify an amount of change (i.e., in a probability) that must be associated with the additional information before the learning engine 110 prompts a user for additional information. As one example, a user may specify that he or she only wants to be prompted for additional information when the additional information increases the probability of the initial diagnosis by at least 20%. Accordingly, when an initial diagnosis has a probability of 40% and this probability would increase to 60% if the additional information were available (e.g., a weight of the patient, a blood pressure of the patient, and the like), the learning engine 110 prompts the user for the additional information. Conversely, when an initial diagnosis has a probability of 30% and this probability would increase to 40% if the additional information were available, the learning engine 110 does not prompt the user. Furthermore, in some embodiments, the learning engine 110 may prompt a user regarding whether the additional information should be obtained. Similarly, in some embodiments, the learning engine 110 directly prompts a user for the additional information. In other embodiments, the learning engine 110 prompts a user for a source of the additional information (e.g., the name of another user or a system storing the additional information).

For example, in some embodiments, the learning engine 110 may generate a set of initial diagnoses (e.g., possible diagnoses) for an image. Based on the set of initial diagnoses, additional information may be determined that would potentially reduce the number of initial diagnoses (e.g., to provide a single or most likely diagnosis). For example, when an initial diagnosis includes a possible syndrome, the learning engine 110 may use additional information to confirm or eliminate the possible syndrome. In particular, the learning engine 110 may prompt a user regarding other detected abnormalities, such as "Are there renal abnormalities?" In some embodiments, the learning engine 110 may also specify a basis for the requested additional information, such as "If renal abnormalities exist, consider Von Hippel Lindau syndrome." Accordingly, a user may understand why the additional information is being requested.

After the additional information is received, the learning engine 110 updates the set of initial diagnoses based on the additional information, such as by reducing the number of diagnoses included in the set or updating a probability of one or more diagnoses included in the set. The set of initial diagnoses, the updated set of diagnoses, or both may be displayed to a user (e.g., with the associated probabilities and optional bases) as a diagnosis. This process may also be repeated (e.g., automatically or in response to a user request) to further refine a diagnosis.

Similarly, in some embodiments, the learning engine 110 may be configured to determine when additional imaging may aid a diagnosis. For example, FIG. 6 illustrates a method 600 performed by the server 102 (i.e., the electronic processor 104 executing instructions, such as the learning engine 110) for automatically analyzing clinical images and determining when additional imaging may aid a diagnosis according to some embodiments.

Figure 6:
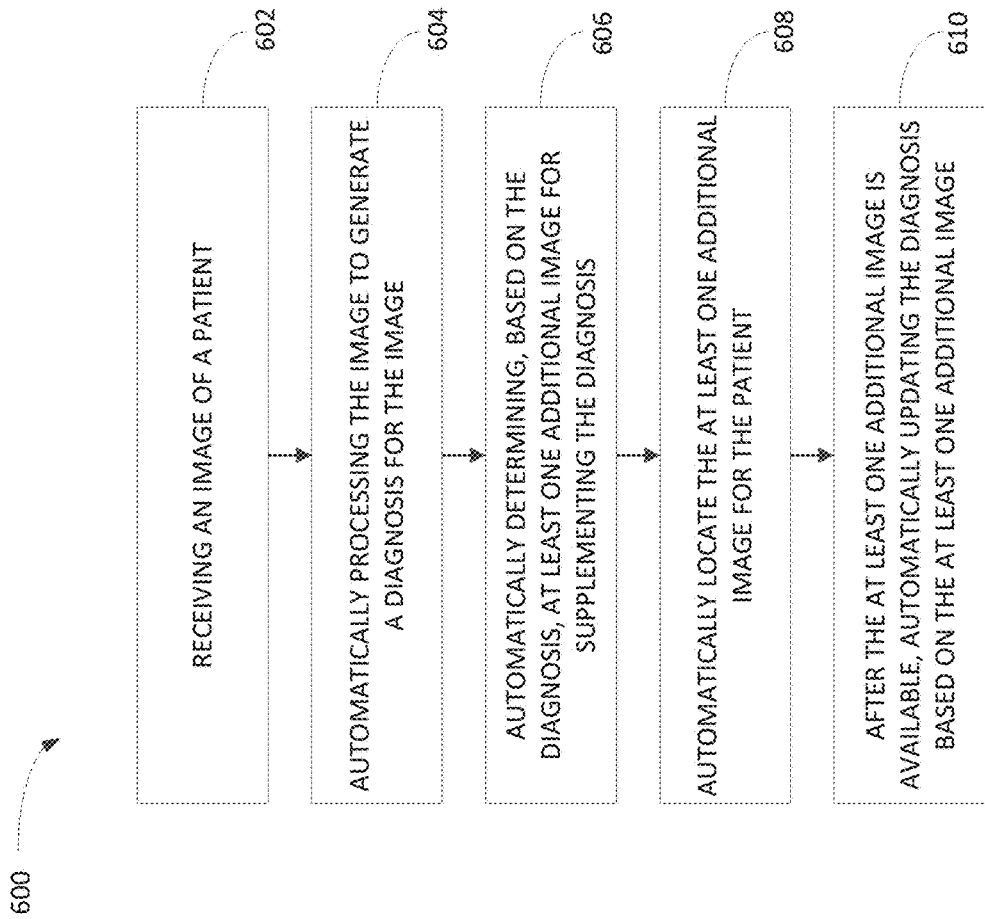
FIG. 6 is a flowchart of a method of automatically analyzing clinical images and determining when additional imaging may aid a diagnosis according to some embodiments.

As illustrated in FIG. 6, the method 600 includes receiving, with the learning engine 110, an image of a patient from at least one data source 112 over an interface (e.g., the input/output interface 108) (at block 602). The method 600 also includes automatically processing the image, with the learning engine 110, to generate a diagnosis for the image (at block 604). In some embodiments, the learning engine 110 generates the diagnosis as described above with respect to FIG. 5.

The learning engine 110 also automatically determines, based on the diagnosis, at least one additional image for supplementing the diagnosis (at block 606) and automatically locates the at least one additional image for the patient (at block 608). For example, when the initial diagnosis is inconclusive findings, the learning engine 110 may apply criteria, such as Appropriate Use Criteria ("AUC"), to determine what other type of imaging is recommended and then query one or more systems storing the determined type of imaging. In some embodiments, the learning engine 110 accesses one or more PACSs, vendor neutral archives, RISs, EMRs, HISs, image study ordering systems, computer assisted detection (CAD) systems, or a combination thereof to locate the additional image. Alternatively or in addition, the learning engine 110 may prompt a user for the additional image (e.g., a storage location or source of the additional image or an indication of whether the additional image has been or will be performed or ordered).

The additional image may be generated before or after the image. When the additional image has not already been performed for a patient, the learning engine 110 may put the diagnosis on hold until the additional image is available. For example, the learning engine 110 may monitor sources of the additional image to detect when the additional image is available. The learning engine 110 may also generate notifications when the additional image remains unavailable after a configurable amount of time. The notifications may be transmitted to one or more users, such as the patient's physician who ordered the initial image. Also, in some embodiments, the learning engine 110 may take one or more automatic actions to obtain the additional image, such as automatically placing an order for the additional image. In some embodiments, the learning engine 110 waits a configurable amount of time before taking any automatic actions.

The at least one additional image may be generated by an imaging modality different than the original image (e.g., original x-ray image followed by a CT scan or MRI). Alternatively or in addition, the at least one additional image may be generated using an imaging parameter different than the original image. As example only, the different imaging parameter may be whether a contrast agent was used, whether a radioactive isotope was used, a time after an agent or isotope was introduced, a MRI pulse sequence, a CT radiation level, or a combination thereof. Also, in some embodiments, the additional image may be performed for a portion of a patient that is the same or different than the portion of the patient represented in the initial image. For example, when an initial diagnosis associated with the initial image effects multiple anatomical structures, the learning engine 110 may use the additional image to determine whether other anatomical structures of the patient (i.e., different from the anatomical structure represented in the initial image) supports or contrasts the potential diagnosis.

As illustrated in FIG. 6, when the additional image is available, the learning engine 110 automatically updates the initial diagnosis based on the additional image (at block 610). In some embodiments, the updated diagnosis includes a differential diagnosis (e.g., a diagnosis distinguishing a particular disease or condition from others that present similar symptoms). In this respect, the learning engine 110 uses the additional image to eliminate some potential diagnoses.

As noted above, in some embodiments, the learning engine 110 is configured to determine relevant images within an image study, relevant portions of an image, or a combination thereof. For example, the learning engine 110 may select a subset of images included in an image study for display to a physician that provide the best view of a particular portion of anatomy or a particular abnormality. For example, the learning engine 110 may identify a multi-planar or a 3-D presentation of a data set (e.g., a volume CT, MRI, PET, or ultrasound data set) that shows an aspect of the anatomy or pathology at a preferred or optimal vantage for a diagnosing physician (e.g., based on a suspected or prior diagnosis). Similarly, within a CT examination including 1000 images, the learning engine 110 may identify 20 images that warrant manual review and may flag these images accordingly. In some embodiments, the learning engine 110 identifies these optimal images or views based on received training information as described above that includes graphical reporting for particular images or views.

Similarly, the learning engine 110 may annotate images to highlight portions of images that the learning engine 110 identifies as being most "important" for manual review. The learning engine 110 may select relevant images or portions of images based on exam indications or probabilities of abnormal findings and common locations for such abnormal findings. Similarly, the learning engine 110 may mark the right paratracheal region on a chest radiograph when abnormalities in this region are frequently missed or when abnormalities likely occur in this region.

Figure 7:
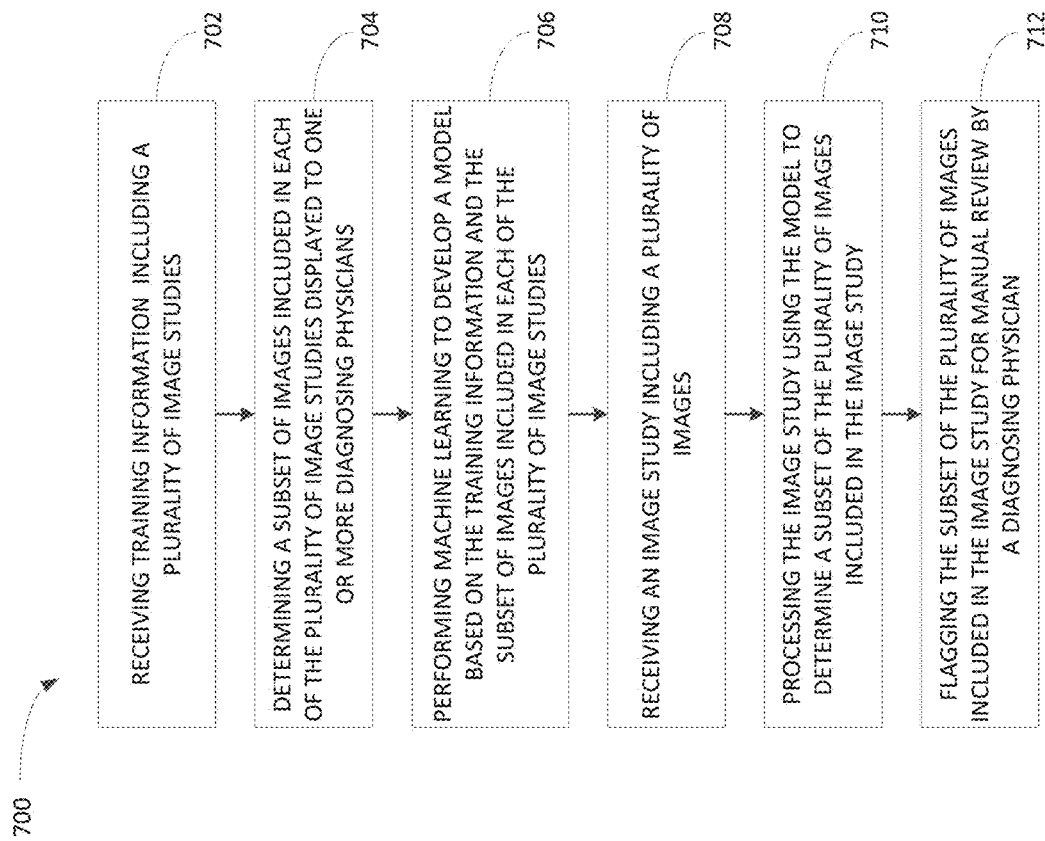
FIG. 7 is a flowchart of a method of automatically determining clinical images within an image study for display to a diagnosing physician according to some embodiments.

For example, FIG. 7 illustrates a method 700 performed by the server 102 (i.e., the electronic processor 104 executing instructions, such as the learning engine 110) for automatically determining clinical images within an image study for display to a diagnosing physician according to some embodiments. As illustrated in FIG. 7, the method 700 includes receiving, with the learning engine 110, training information from at least one data source 112 over an interface (e.g., the input/output interface 108), wherein the training information includes a plurality of image studies (at block 702). The method 700 also includes determining, with the learning engine 110, a subset of images included in each of the plurality of image studies displayed to one or more diagnosing physicians (at block 704) and performing, with the learning engine 110, machine learning to develop a model based on the training information and the subset of images included in each of the plurality of image studies (at block 706). In some embodiments, the learning engine 110 develops the models as described above with respect to FIGS. 2 and 5.

In some embodiments, the learning engine 110 determines subset of images included in the training information that were displayed to a diagnosing physician based on what images included in an image study were associated with an annotation. The annotation may include a graphical marker designating a portion of an image as described above. In other embodiments, the annotation may include other forms of diagnostic information associated with an image. Accordingly, in some embodiments, the determined subset of images included in an image study includes at least two images of the same anatomical structure of a patient obtained at different times during an imaging procedure. The learning engine 110 may store image characteristics for the determined subset of images in a data structure and may use the data structure (e.g., as part of developing the model) to identify image characteristics associated with images commonly reviewed by a diagnosing physician (i.e., clinically-relevant images). Accordingly, the learning engine 110 may identify a subset of images within an image study having image characteristics that help a diagnosing physician review the image study efficiently and effectively.

In particular, as illustrated in FIG. 7, after developing the model (at block 706), the method 700 includes receiving, with the learning engine 110, an image study including a plurality of images (at block 708) and processing the image study, with the learning engine 110, using the model to determine a subset of the plurality of images included in the image study (at block 710). The learning engine 110 flags the determined subset of the plurality of images included in the image study for manual review by a diagnosing physician (at block 712).

In some embodiments, the flagged subset is used when the image study is opened or displayed within an image review application (e.g., by a diagnosing physician). For example, when the image study is displayed within the image review application, the flagged subset may be graphically marked (e.g., using an icon or other distinguishing feature). Also, in some embodiments, the flagged subset of the plurality of images may be displayed within the image review application before displaying a remainder of the plurality of images included in the image study. Alternatively, only the flagged subset of the plurality of images may be displayed within the image review application.

In addition, in some embodiments, the learning engine 110 assigns a priority to images included in a flagged subset. The priority may be based on the frequency at which images with particular image characteristics are displayed to a diagnosing physician. For example, the learning engine 110 may assign an image having image characteristics that are displayed 90% of the time (as learned from the training information) a higher priority than an image having image characteristics that are displayed 70% of the time. When the image study is displayed within an image review application, the images included in the flagged subset may be displayed in an order based on their assigned priorities (e.g., higher priority images displayed before lower priority images). Similarly, in some embodiments, only images with a priority above a configurable threshold may be initially displayed or displayed at all. In some embodiments, the learning engine 110 may similarly assign a priority to an overall image study based on the flagged subset of images (e.g., as a composite priority based on the priorities for individual images, as a priority based on a number of images included in the flagged subset, and the like). The priority assigned to the image study may be used to schedule an image study for manual review. For example, an image study with fewer flagged images may be easier or harder to complete than an image study with more flagged images. Also, in some embodiments, the priorities assigned to image studies may be used to schedule the studies based on the work schedule of a diagnosing physician. For example, diagnosing physicians may be more focused at certain times of the day and, hence, image studies with priorities satisfying a particular threshold (e.g., greater than or less than a threshold) may be schedule during this time if they likely require more manual review than other image studies.

The learning engine 110 may also be configured to perform a similar method to determine portions of a single image to display to a diagnosing physician. For example, FIG. 8 illustrates a method 800 performed by the server 102 (i.e., the electronic processor 104 executing instructions, such as the learning engine 110) for automatically determining portions of clinical images for display to a diagnosing physician according to some embodiments.

Figure 8:
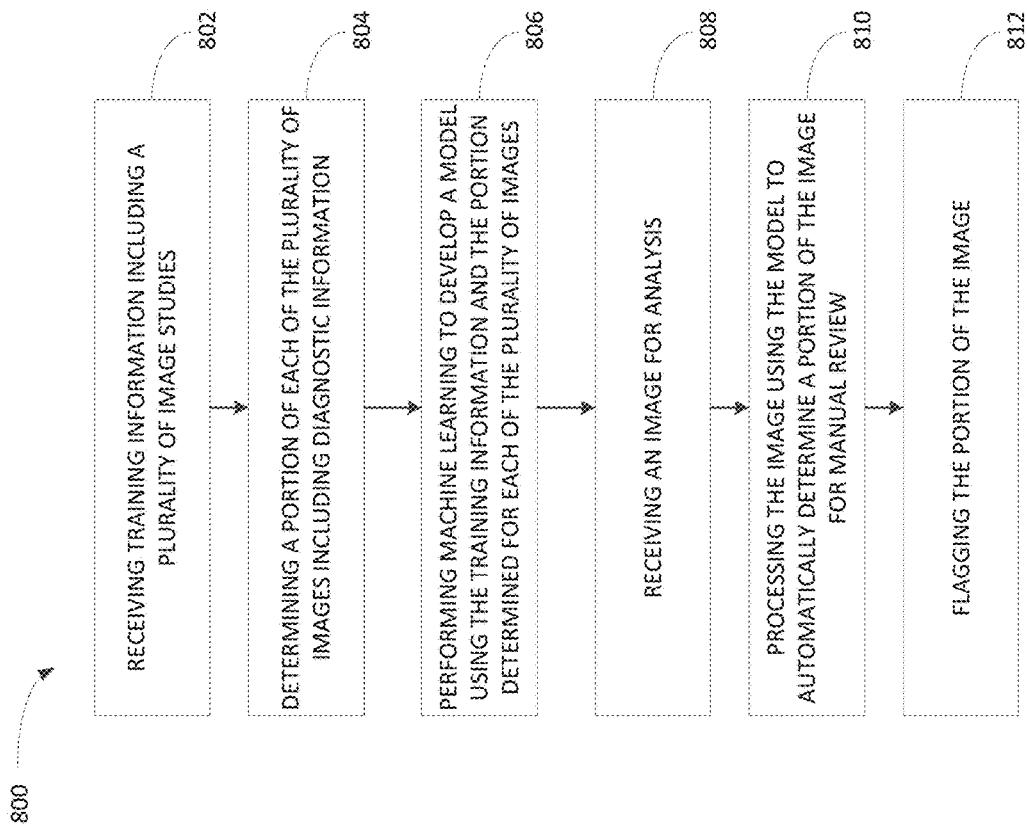
FIG. 8 is a flowchart of a method of automatically determining portions of clinical images for display to a diagnosing physician according to some embodiments.

As illustrated in FIG. 8, the method 800 includes receiving, with the learning engine 110, training information from at least one data source 112 over an interface (e.g., the input/output interface 108) (at block 802). The training information includes a plurality of images (at block 802). The method 800 also includes determining, with the learning engine 110, a portion of each of the plurality of images including diagnostic information (at block 804) and performing, with the learning engine 110, machine learning to develop a model using the training information and the portion determined for each of the plurality of images (at block 806). As described above with respect to the method 700, the learning engine 110 may determine the portion of each of the plurality of images based on an annotation (e.g., a graphical marker) included in an image.

The method 800 also includes receiving, with the learning engine 110, an image for analysis (at block 808), processing, with the learning engine 110, the image using the model to automatically determine a portion of the image for manual review (at block 810), and flagging, with the learning engine 110, the portion of the image (at block 812). In some embodiments, multiple portions of an image may be flagged or no portions of an image may be flagged (e.g., when an image does not include a relevant portion).

As described above with respect to the method 700, the flagged portion of the image may be used when the image is displayed within an image review application. For example, an image review application may graphically mark the flagged portion of the image when the image is displayed (e.g., using a graphical marker as described above), may preferentially display the flagged portion of the image when the image (e.g., centered within a window displaying the image), or may display the image with the flagged portion of the image in a preferential format as compared to an image without a flagged portion. Also, in some embodiments, the learning engine 110 assigns a priority to an image based on the flagged portion of the image. The priority may designate an order of display of the images within an image review application. Similarly, the priority assigned to an image may be used to schedule the image for manual review (or schedule the image study including the image). Also, when the image is included in an image study, the image with the flagged portion may be prioritized (e.g., displayed before) other images included in the image study (e.g., images not including a flagged portion) when the image study is displayed for review.

In some embodiments, the learning engine 110 may apply rules when processing images. For example, as noted above, the learning engine 110 may develop different models for different types of anatomy. The learning engine 110 may similarly develop different models for different types of images (e.g., ECG data, ultrasounds, CT scans, sonograms, and the like). Accordingly, the learning engine 110 may apply rules to pre-process a received image to identify what models should be applied to the image. For example, in some embodiments, the learning engine 110 may pre-process a received image using associated clinical and historical information to identify what abnormalities may be found in the image.

In some embodiments, a user may set or modify the rules applied by the learning engine 110. For example, a physician may be able to specify what particular models should be applied to a particular type of image. For example, when a CT scan is performed, the learning engine 110 may be configured (e.g., through a rule) to check for internal bleeding and provide a "yes" or "no" diagnose (e.g., in addition to performing other types of diagnoses relevant for a CT scan and the particular type of anatomy captured in the image). Similarly, the learning engine 110 may be configured (e.g., through a rule) to focus on a particular portion of an image or a particular type of diagnosis that is commonly missed during manual review. These rules may be set at a particular user level (e.g., the physician that submitted the image for automatic processing, the diagnosing physician, the patient, and the like), a clinic level (e.g., all images submitted from a particular hospital or imaging center), a network level (e.g., all images submitted from hospitals and imaging centers associated with a particular health care network or service provider, such as Anthem or Athena), or a system-wide level (e.g., all images submitted for automatic analysis).

Figure 9:
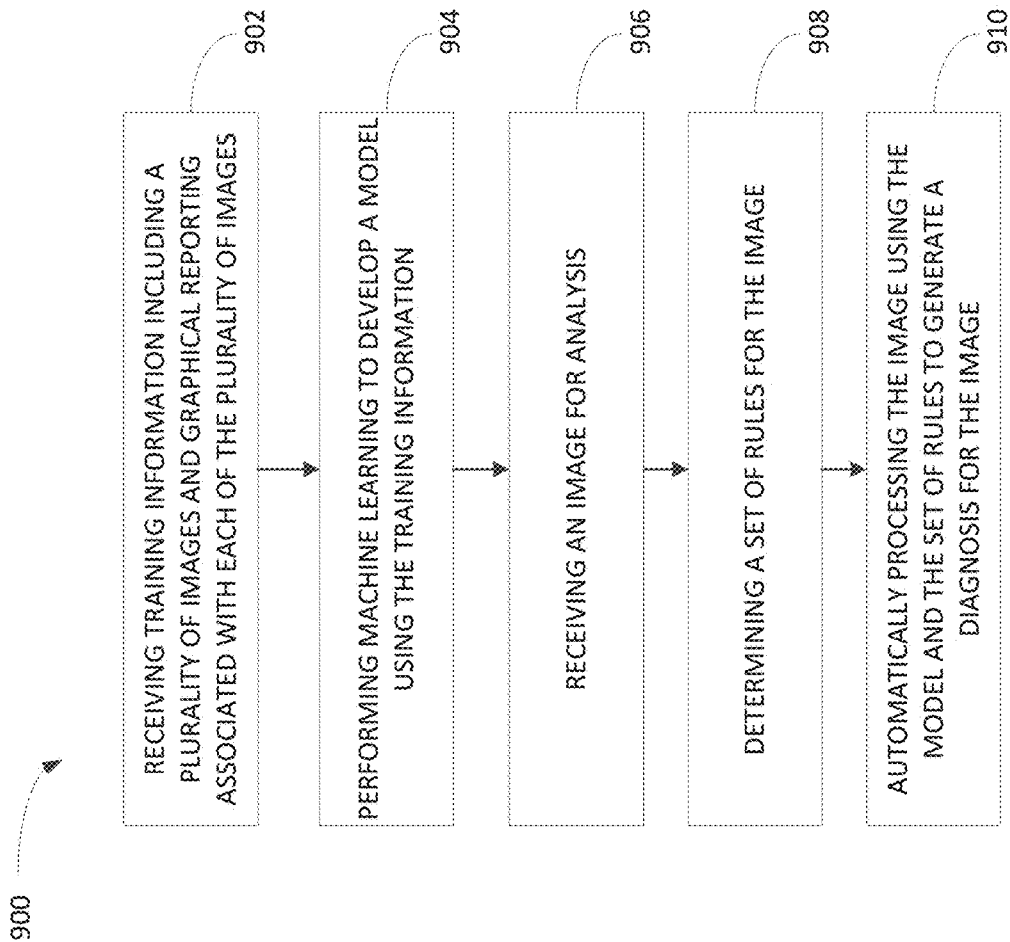
FIG. 9 is a flowchart of a method of automatically analyzing clinical images using rules and image analytics developed using graphical reporting associated with previously-analyzed clinical images according to some embodiments.

For example, FIG. 9 illustrates a method 900 performed by the server 102 (i.e., the electronic processor 104 executing instructions, such as the learning engine 11) for automatically analyzing clinical images using rules and image analytics developed using graphical reporting associated with previously-analyzed clinical images according to some embodiments. As illustrated in FIG. 9, the method 900 includes receiving, with the learning engine 110, training information from at least one data source 112 over an interface (e.g., the input/output interface 108) (at block 902). As described above with respect to methods 200 and 500, the training information includes a plurality of images and graphical reporting associated with each of the plurality of images. The graphical reporting includes a graphical marker designating a portion of an image and diagnostic information associated with the marked portion of the image. As illustrated in FIG. 9, the method 900 also includes performing, with the learning engine 110, machine learning to develop a model using the training information (at block 904).

The method 900 also includes receiving, with the learning engine 110, an image for analysis (at block 906), determining, with the learning engine 110, a set of rules for the image (at block 908), and automatically processing, with the learning engine 110, the image using the model and the set of rules to generate a diagnosis for the image (at block 910). As described above, the learning engine 110 may determine the set of rules based, for example, on a user viewing the image within an image review application, a diagnosing physician performing a diagnosis of the image, a physician ordering an image procedure during which the image was generated, an organization of diagnosing physicians associated with the image, an organization of healthcare facilities associated with the image, an organization associated with a workstation displaying the image, an imaging modality generating the image, or an image acquisition site associated with the image. Alternatively or in addition, the learning engine 110 may determine the set of rules based on patient demographic information associated with the image, a type of the image or a type of an imaging exam associated with the image, a geographic location associated with the image (e.g., a location where the image was taken or a location of the patient), or a geographical location of a diagnosing physician associated with the image. Also, in some embodiments, the learning engine 110 may determine the set of rules based on applicable epidemic information. Furthermore, in some embodiments, the learning engine 110 determines an anatomical structure represented in the image and determines the set of rules based on the anatomical structure.

In some embodiments, the learning engine 110 automatically generates the rules. For example, the learning engine 110 may use training information associated with a particular user, facility, organization, and the like to automatically learn applicable rules. Alternatively or in addition, the learning engine 110 may receive manually-defined rules from a user. For example, in some embodiments, the learning engine 110 (or a separate device or piece of software) may be configured to generate a graphical user interface that displays a set of rules (whether automatically or manually defined) and allows a user to modify the set of rules.

As described above, the learning engine 110 may update the developed models based on new training information, feedback regarding the performance of the models, or a combination thereof. For example, after generating a diagnosis for an image, the learning engine 110 may collect information from one or more sources (e.g., pathology reports or other laboratory reports) to identify whether the generated diagnosis was correct. When the diagnosis was not correct, the learning engine 110 may update the one or more models used to generate the diagnosis (e.g., by making an adjustment to the model, by re-developing the model using the updated training information, or by another technique for updating models).

The learning engine 110 may similarly use this feedback to perform outcome analytics. For example, when pathology results are available for particular images, the learning engine 110 may track how well the images were analyzed (e.g., automatically or manually by a diagnosing physician). The learning engine 110 may use this information to determine how well the models or a physician or a group of physicians are performing particular diagnoses (e.g., detecting cancer). For example, the learning engine 110 may be configured to determine how well a particular physician or group of physicians is performing as compared to other physicians, groups of physicians, or national or worldwide averages.

The learning engine 110 may also be configured to use this information to perform analytics to determine parameters influencing a correct diagnosis or an incorrect diagnosis, such as a number and the types of images taken, the imaging equipment, and the like. For example, the learning engine 110 may capture information from DICOM header files and detect correlations between particular imaging parameters and correct or incorrect diagnoses (e.g., using a multivariate data analysis).

Similarly, the learning engine 110 may be configured to monitor and report diagnostic patterns and trends. For example, one diagnosing physician reading chest x-rays in an institution may diagnose congestive heart failure at a greater incidence than another diagnosing physician. Accordingly, the learning engine 110 may use this information to identify which diagnosing physician is correct, identify diagnosing physicians needing further training or supervision, identify diagnosing physicians to act as an "expert" for reviewing particular images (e.g., images identified as being "indeterminate" by the learning engine 110), or identify training information that should be assigned a greater weight by the learning engine 110. For example, in some embodiments, the learning engine 110 may (e.g., automatically) schedule training for a diagnosing physician or a group of diagnosing physicians when an associated score falls below a configurable threshold. The learning engine 110 may also use this information to provide closed feedback loops to particular physicians or facilities. For example, the learning engine 110 may provide statistics such as "94% of chest x-rays ordered from this clinic this month were normal," or "99% of your ordered ankle x-rays showed no fracture, the average for this clinic is 85%," which physicians and facilities may use to identify areas for improvement. Similarly, the learning engine 110 may be configured to detect a trend, such an increase in particular diagnoses, an identification of a population of patients associated with a particular diagnosis, an epidemic, or an underlying cause for a particular diagnosis (e.g., Legionnaire's disease). Thus, the learning engine 110 may use feedback to perform audits, determine quality of care, determine payment and reimbursement rates, allocate human resources, or a combination thereof.

Figure 10:
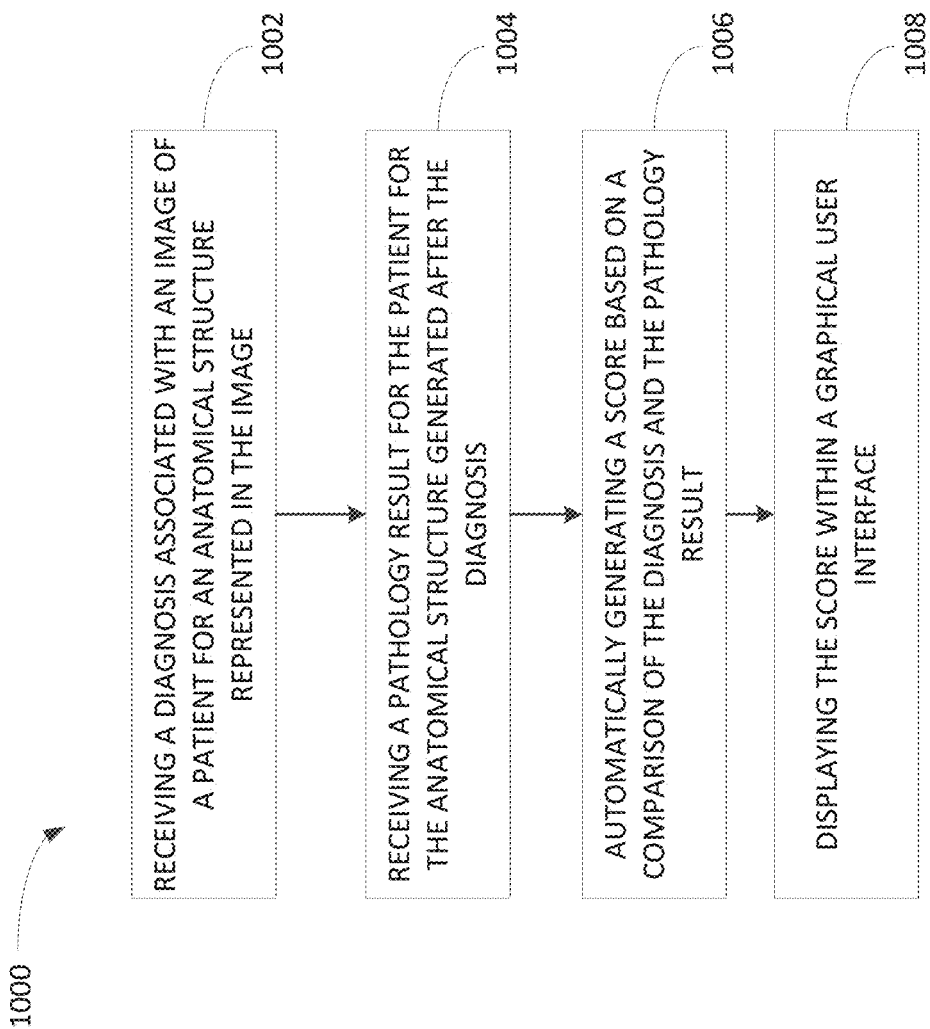
FIG. 10 is a flowchart of a method of automatically scoring diagnoses associated with clinical images according to some embodiments.

For example, FIG. 10 illustrates a method 1000 performed by the server 102 (i.e., the electronic processor 104 executing instructions, such as the learning engine 110) for automatically scoring diagnoses associated with clinical images according to some embodiments. As illustrated in FIG. 10, the method 1000 includes receiving, with the learning engine 110, a diagnosis associated with an image of a patient from at least one data source over an interface (e.g., the input/output interface 108) (at block 1002). The diagnosis relates to an anatomical structure represented in the image. The diagnosis may be a manual diagnosis generated by a diagnosing physician, an automatic diagnosis generated by a computer system (e.g., the learning engine 110), or a combination thereof.

The method 1000 also includes receiving, with the learning engine 110, a pathology result for the patient (e.g., from at least one pathology result source) for the anatomical structure over an interface (e.g., the input/output interface 108) (at block 1004). In some embodiments, the pathology result was generated after the received diagnosis. The method 1000 also includes automatically generating, with the learning engine 110, a score based on a comparison of the diagnosis and the pathology result (at block 1006). The method 1000 may also include displaying, with the learning engine 110, the score within a graphical user interface (at block 1008).

The learning engine 110 may generate a score for an individual diagnosing physician, a plurality of diagnosing physicians, an individual facility, a network of a plurality of facilities, or another configurable population. For example, in some embodiments, the learning engine 110 generates a score for itself or another computer system configured to automatically generate diagnoses. In some embodiments, the learning engine 110 displays a score within a graphical interface that includes a plurality of scores, such as a score for each of a plurality of individual diagnosing physicians. In some embodiments, the learning engine 110 ranks the displayed scores (e.g., highest score to lowest score).

The learning engine 110 may generate a score that includes a percentage of diagnoses not matching the corresponding pathology result, a percentage of diagnoses matching the corresponding pathology result, or both. Also, in some embodiments, the learning engine 110 generates a score that compares one diagnosing physician to another diagnosing physician or to a base score (e.g., representing a normal or acceptable amount of error). For example, in some embodiments, the learning engine 110 generates a score that compares the performance of a diagnosing physician to performance of a computer system configured to automatically generate diagnoses. The learning engine 110 may also be configured to generate a score for a particular type of imaging modality, a particular type of the image or a particular type of imaging exam associated with the image, a particular geographic location, a particular time of day, a particular type or population of patients, or a combination thereof. Also, in some embodiments, the learning engine 110 may generate a score based on one or more configurable preferences (e.g., associated with a user, a group of users, or the like).

As noted above, when the original diagnosis was automatically generated by a computer system, such as the learning engine 110, the computer system may be updated based on the score. For example, the learning engine 110 may use a score to determine when to perform an updates. Similarly, the learning engine 110 may use a score to assign a weight to particular training information as described above.

In some embodiments, the learning engine 110 may also be configured to aid a diagnosing physician in difficult activities, such as identifying particular abnormalities that are commonly missed by diagnosing physicians. For example, when analyzing a submitted image, the learning engine 110 may be configured to screen chest x-rays and chest CT scans for pulmonary nodules measuring less than a configurable size that are commonly missed by diagnosing physician. Similarly, the learning engine 110 may be configured to screen thyroid glands, skin, and subcutaneous tissues for abnormalities on a chest CT scan when diagnosing physicians commonly miss lesions in these locations. As another example, the learning engine 110 may be configured to focus on particular regions of an image or particular abnormalities that a particular diagnosing physician commonly misses (e.g., a known blind spots or bias of a particular physician). In some embodiments, a diagnosing physician may manually specify (e.g., through one or more rules) aids for particular activities. However, in other embodiments, the learning engine 110 may be configured to automatically identify common errors for individual physicians or populations of physicians.

Figure 11:
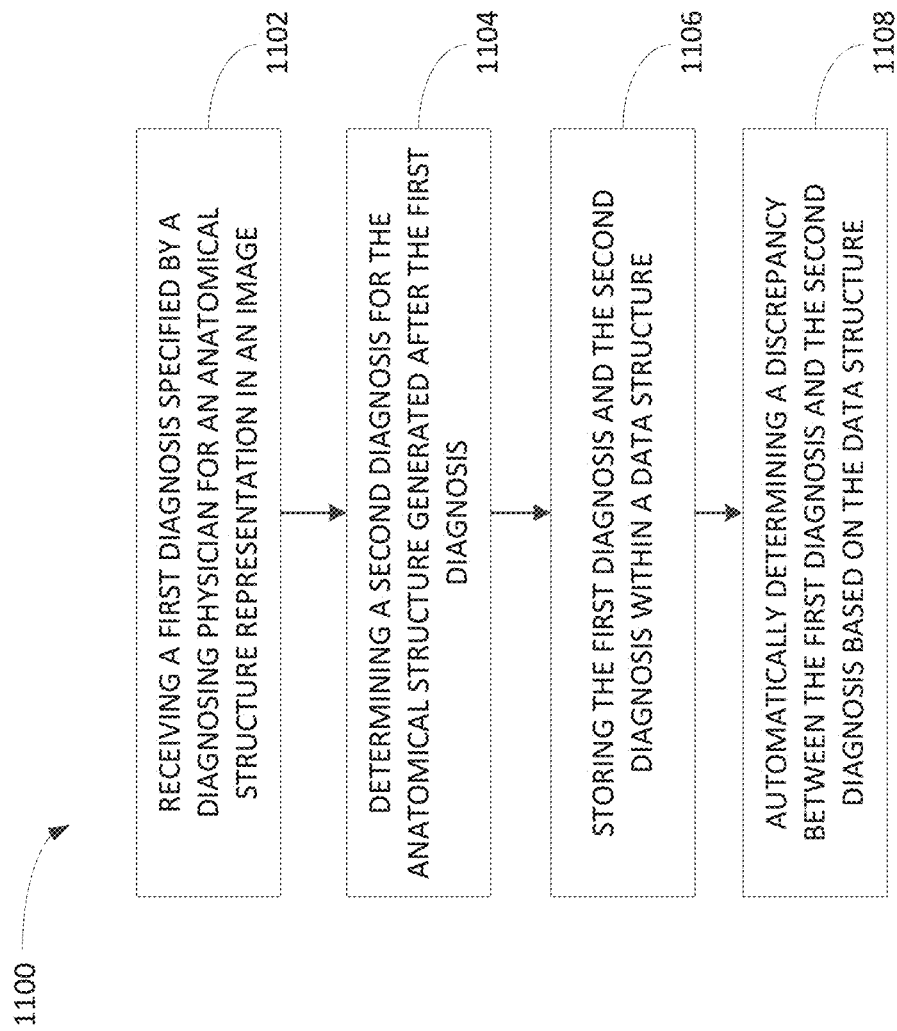
FIG. 11 is a flowchart of a method of automatically determining diagnosis discrepancies for clinical images according to some embodiments.

For example, FIG. 11 illustrates a method 1100 performed by the server 102 (i.e., the electronic processor 104 executing instructions, such as the learning engine 110) for automatically determining diagnosis discrepancies for clinical images according to some embodiments. As illustrated in FIG. 11, the method 1100 includes receiving, with the learning engine 110, a first diagnosis from at least one data source 112 over an interface (e.g., the input/output interface 108) (at block 1102). The first diagnosis relates to an anatomical structure represented in an image. In some embodiments, the first diagnosis is a diagnosis manually specified by a diagnosing physician. The method 1100 also includes determining, with the learning engine, a second diagnosis for the anatomical structure generated after the first diagnosis (at block 1104). In some embodiments, the second diagnosis includes a pathology report for the anatomical structure, a diagnosis associated with additional imaging of the anatomical structure (i.e., different from the image associated with the first diagnosis), a computer-generated diagnosis associated with an image (e.g., the same image associated with the first diagnosis or a different image), a laboratory finding, an electronic medical record (EMR), or a combination thereof.

As illustrated in FIG. 11, the learning engine 110 stores the first diagnosis and the second diagnosis within a data structure (e.g., a table) (at block 1106) and uses the data structure to automatically determine a discrepancy between the first diagnosis and the second diagnosis (at block 1108).

In some embodiments, the learning engine 110 may generate a report based on the data structure. The report may be for the diagnosing physicians or a plurality of diagnosing physician including the diagnosing physician. The report may include the discrepancy, which may be represented as an occurrence rate associated with the discrepancy (e.g., how frequently a diagnosing physician provides a diagnosis that does not match with a later diagnosis). In some embodiments, the report is parsable (e.g., sortable, filterable, and the like), such as by an imaging modality, a diagnosing physician, an exam type, an image type, an anatomical structure, patient demographic information, or a date.

In addition to or as an alternative to generating a report, the learning engine 110 may generate one or more electronic notifications based on the data structure or a particular discrepancy identified based on the data structure. The learning engine 110 may send the notification to one or more users or systems, such as the diagnosing physician that generated a first diagnosis. In some embodiments, the electronic notification includes an e-mail message, a page, an instant message, or the like. Also, in some embodiments, the learning engine 110 generates and sends electronic notifications based on one or more configurable preferences (e.g., of the diagnosing physician associated with the discrepancy).

In addition to or as an alternative to generating a report or generating electronic notifications, the learning engine 110 may graphical mark a portion of the image associated with a first diagnosis based on the discrepancy. For example, when a diagnosing physician misses an anomaly within the image as part of the first diagnosis that is detected as part of the second diagnosis, the learning engine 110 may be configured to automatically mark the missed anomaly within the image. By marking the anomaly, the diagnosing physician that missed the anomaly can review the image to learn from his or her mistakes.

Similarly, in some embodiments, the learning engine 110 applies the data structure to new images being reviewed by a diagnosing physician. For example, when a new image is received for review by a particular diagnosing physician, the learning engine 110 may automatically graphically mark one or more portions of the new image based on the data structure. The learning engine 110 may graphically mark the new image by marking a detected anomaly within the new image, one or more portions of the new image that may potentially include the anomaly, or a combination thereof. For example, when a particular diagnosing physician (or a population of diagnosing physicians) commonly misses anomalies in a particular portion of a lung, the learning engine 110 may automatically mark this portion on the image to draw the diagnosing physician's attention to the portion. Accordingly, when a diagnosing physician is reviewing the new image to provide a diagnosis, the diagnosing physician is alerted to previous discrepancies to mitigate future discrepancies.

In addition to or as an alternative to providing the graphical markings, the learning engine 110 may automatically display a warning with the new image based on the data structure to alert the diagnosing physician of previous discrepancies to mitigate future discrepancies. The graphical marking, the warnings, or both may be configurable based on one or more preferences of a user. For example, a user may be able to enable or disable the graphical markings, the warnings, or both.

Similarly, as described above, a particular diagnosing physician may (subconsciously) develop a bias. For example, after diagnosing five cases of breast cancer, a diagnosing physician may be reluctant to make a further diagnosis of breast cancer. Similarly, a particular diagnosing physician may be less likely to correctly diagnosis a particular abnormality for a particular population of patients or under certain reading conditions.

Figure 12:
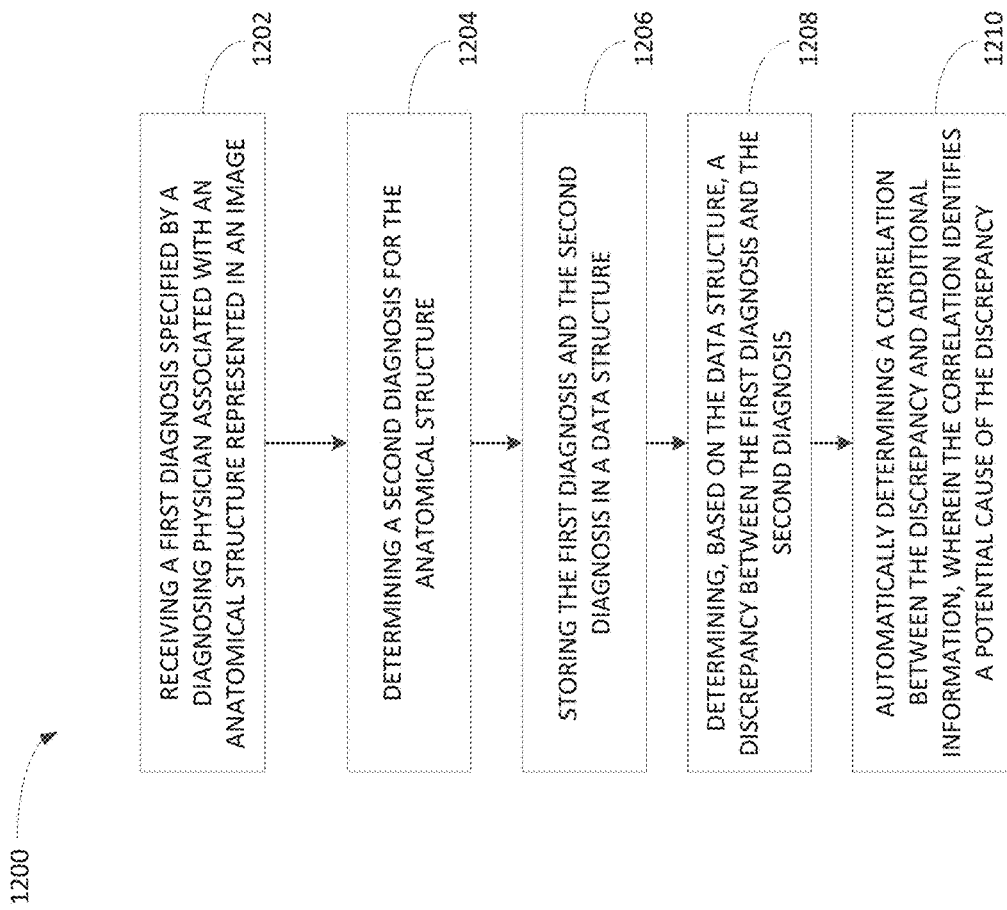
FIG. 12 is a flowchart of a method of automatically determining a potential bias of a diagnosing physician according to some embodiments.

Accordingly, FIG. 12 illustrates a method 1200 performed by the sever 102 (i.e., the electronic processor 104 executing instructions, such as the learning engine 110) for automatically determining a potential bias of a diagnosing physician according to some embodiments. As illustrated in FIG. 12, the method 1200 may include receiving, with the learning engine 110, a first diagnosis specified by the diagnosing physician from at least one data source 112 over an interface (e.g., the input/output interface 108) (at block 1202). The first diagnosis may be associated with an anatomical structure represented in an image. The method 1200 also includes determining, with the learning engine 110, a second diagnosis for the anatomical structure (at block 1204) and storing, with the learning engine 110, the first diagnosis and the second diagnosis in a data structure (at block 1206). The learning engine 110 also determines, based on the data structure, a discrepancy between the first diagnosis and the second diagnosis (at block 1208) and automatically determines a correlation between the discrepancy and additional information (at block 1201). As described in more detail below, the correlation may identify a potential cause of the discrepancy.

The additional information may include a time of day of the first diagnosis or a day of the week of the first diagnosis. Accordingly, the learning engine 110 may determine a correlation between a bias of the diagnosing physician and a particular time of the day or day of the week. Alternatively or in addition, the additional information may include patient demographic information associated with the first diagnosis, such as, for example, a patient's age, race, or gender. Thus, the learning engine 110 may determine a correlation between a bias of the diagnosing physician and a particular diagnosis for a particular type of patient. Alternatively or in addition, the additional information may include at least one diagnosis specified by the diagnosing physician prior to the first diagnosis (e.g., during a reading session including the first diagnosis or another configurable period of time prior to the first diagnosis). Accordingly, the learning engine 110 may determine a correlation between a bias of the diagnosing physician and a particular reading schedule or sequence of prior diagnoses. For example, the additional information may include an amount of time between the first diagnosis and a third diagnosis specified by the diagnosing physician prior to the first diagnosis matching the first diagnosis. Thus, the learning engine 110 may determine a correlation between a bias of the diagnosing physician and a prior frequency or sequence of similar diagnoses (e.g., less inclined to render an abnormal diagnosis after five or more abnormal diagnoses were previously rendered).

The additional information may also include information associated with the image used to generate the first diagnosis, such as an imaging modality associated with the first diagnosis, or an imaging acquisition site associated with the first diagnosis. Accordingly, the learning engine 110 may determine a correlation between particular diagnosis and particular imaging information. In other embodiments, the additional information may include an anomaly or anatomical structure identified as part of the first diagnosis or the second diagnosis that may represent a bias of a diagnosing physician toward particular anomalies or particular anatomical structures. Similarly, the additional information may include a geographic location of the diagnosing physician or a patient associated with the first diagnosis or a reading condition of the diagnosing physician associated with the first diagnosis, such as a workstation configuration, a number of diagnosing physicians, or a resolution of the workstation.

The learning engine 110 may use a determined correlation in various ways. For example, in one embodiment, the learning engine 110 may generate a report based on one or more determined correlations (e.g., to report on identified biases for one or more diagnosing physicians and optionally one or more recommendations for addressing the biases). Alternatively or in addition, when a new image is received for analysis, the learning engine 110 may process the new image to determine whether a determined correlation exists for the new image and, if so, automatically display a warning to a diagnosing physician regarding the correlation (e.g., while displaying the second image within an image review application). For example, when the learning engine 110 determines a correlation between a bias of a diagnosing physician and the prior five diagnoses generated by the diagnosing physician, the learning engine 110 may display a warning why the prior five diagnoses of the diagnosing physician satisfy the correlation to help prevent the diagnosing physician from allowing previous diagnoses to impact a current diagnosis.

Similarly, when a new image is received for analysis and the correlation exists for the new image, the learning engine 110 may graphically mark the new image to indicate a portion of the new image that may potentially lead to a discrepancy based on the correlation. For example, when the learning engine 110 determines a correlation between a bias of a diagnosing physician and a particular abnormality within a particular region of a lung, the learning engine 110 may add a graphical mark to new images of the lung to mark the biased region of the lung. In some embodiments, the learning engine 110 may vary one or more characteristics of a graphical mark (e.g., color, size, shape, animation, etc.) to indicate a type of the correlation associated with the graphical mark (e.g., a patient correlation, a time correlation, a prior diagnosis correlation, or an anatomical correlation). Also, in some embodiments, the learning engine 110 may vary one or more characteristics of a graphical mark based one or more configurable preferences (e.g., of a user). In particular, in some embodiments, the preferences may allow a user to enable or disable the graphical marks. Also, in some embodiments, when a user selects a graphical mark, the learning engine 110 displays additional information regarding the correlation, such as a warning as described above.

In some embodiments, the learning engine 110 may also be configured to automatically monitor the results of various imaging protocols and associated clinical behavior. For example, the learning engine 110 may be configured to automatically identify that in a body MRI protocol or a particular series of images is never viewed by a physician or is routinely diagnosed as being "normal." Based on this information, the learning engine 110 may recommend or automatically make changes to a procedure to eliminate a particular series from the procedure, which reduces radiation and data processing requirements. Similarly, when a particular series in an imaging procedure is routinely diagnosed as being "abnormal," the learning engine 110 may prioritize this series (e.g., for automatic processing, for manual review, or both).

Figure 13:
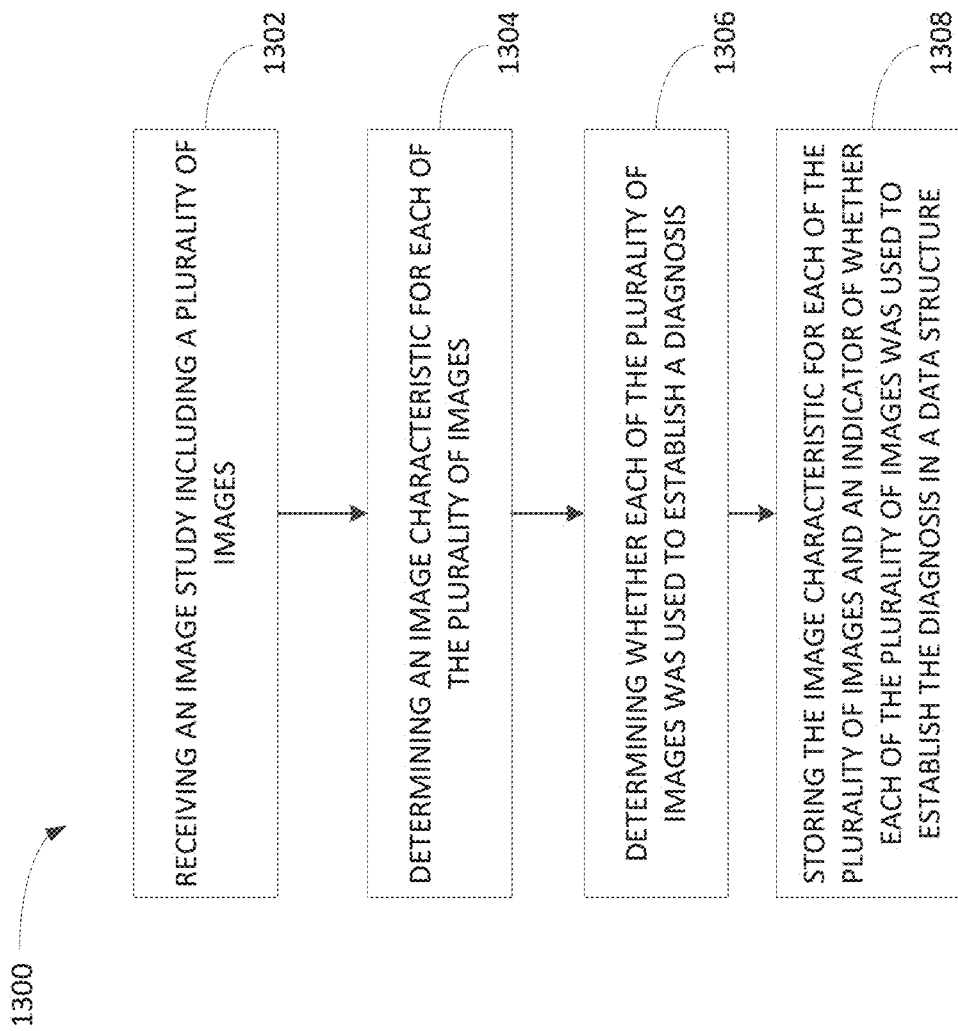
FIG. 13 is a flowchart of a method of automatically determining image characteristics serving as a basis for a diagnosis associated with an image study type according to some embodiments.

For example, FIG. 13 illustrates a method 1300 performed by the sever 102 (i.e., the electronic processor 104 executing instructions, such as the learning engine 110) for automatically determining image characteristics serving as a basis for a diagnosis associated with an image study type according to some embodiments. As illustrated in FIG. 13, the method 1300 includes receiving, with the learning engine, an image study from at least one data source 112 over an interface (e.g., the input/output interface 108) of the image study type (i.e., is a particular type of image study) (at block 1302). The image study includes a plurality of images. As illustrated in FIG. 13, the method 1300 also includes the determining, with the learning engine 110, an image characteristic for each of the plurality of images included in the received image study (at block 1304). The image characteristic may include, for example, an anatomical structure, whether a contrast agent was used or a radioactive isotope was used, a time after a contrast agent or a radioactive isotope was introduced, an orientation, an image acquisition parameter, DICOM header information, or a combination thereof.

The method 1300 also includes determining, with the learning engine 110, whether each of the plurality of images was used to establish a diagnosis (at block 1306). The learning engine 110 may determine whether an image was used to establish a diagnosis by determining whether the image includes an annotation, such as a graphical marker as described above or other diagnostic information. Alternatively or in addition, the learning engine 110 may determine whether an image was used to establish a diagnosis by determining whether the image was displayed to a diagnosing physician rendering the diagnosis during a reading session of the diagnosing physician. Further yet, the learning engine 110 may determine whether an image was used to establish a diagnosis by determining whether the image was diagnosed as normal.

As illustrated in FIG. 13, the method 1300 also includes storing, with the learning engine 110, the image characteristic for each of the plurality of images and an indicator of whether each of the plurality of images was used to establish the diagnosis in a data structure (at block 1308). The learning engine 110 may use the generated data structure in various ways. For example, the learning engine 110 may automatically determine a frequency of an image with a particular image characteristic being included in a particular type of image study (e.g., this type of image is only included in this type of image study 50% of the time). Similarly, the learning engine 110 may automatically determine a frequency of an image with a particular image characteristic being used to establish a diagnosis. For example, the learning engine 110 may determine a frequency of an image with a particular image characteristic including an annotation or not including an annotation, being displayed to a diagnosing physician or not being displayed to a diagnosing physician, or being diagnosed as normal or not normal. The learning engine 110 may use these frequencies to generate a report. For example, the learning engine 110 may generate a report that includes a plurality of frequencies associated with different image characteristics, such as frequencies satisfying one or more configurable thresholds (e.g., image characteristics being clinically-relevant at least 80% of the time or less than 50% of the time). The plurality of frequencies may be associated with the same image study type or multiple image study types. Also, in some embodiments, the report may be parsable, such as by an imaging modality, a diagnosing physician, an anatomical structure, patient demographic information, or a date.

The learning engine 110 may also use the data structure to modify a subsequent image study of the image study type. For example, when images with particular image characteristics are rarely or never reviewed, the learning engine 110 may automatically eliminate those images from an image study (e.g., modify imaging parameters or discard images included in a generated image study). The learning engine 110 may also use the data structure to process subsequent image studies of the image study type. For example, when a new image study of the image study type is received, the learning engine 110 may prioritize images included in the study based on the data structure. In particular, the learning engine 110 may display images routinely serving as a basis for a diagnosis before images rarely serving as a basis for a diagnosis to improve efficiency and accuracy. Similarly, depending on what images are included in a received image study, the learning engine 110 may use the data structure to prioritize image studies for review.

The functionality described above with respect to the learning engine 110 has applicability in many areas of healthcare. For example, the learning engine 110 may be used in orthopedic medicine. In particular, the learning engine 110 may be configured to automate implant planning, which provides time savings for both orthopedic surgeons and implant manufacturers involved in the implant planning process. In particular, orthopedic practices are typically driven by their bottom line efficiency and the number of surgeries that may be performed per week. Therefore, automating portions of this practice may improve efficiencies in orthopedic practices.

Figure 14:
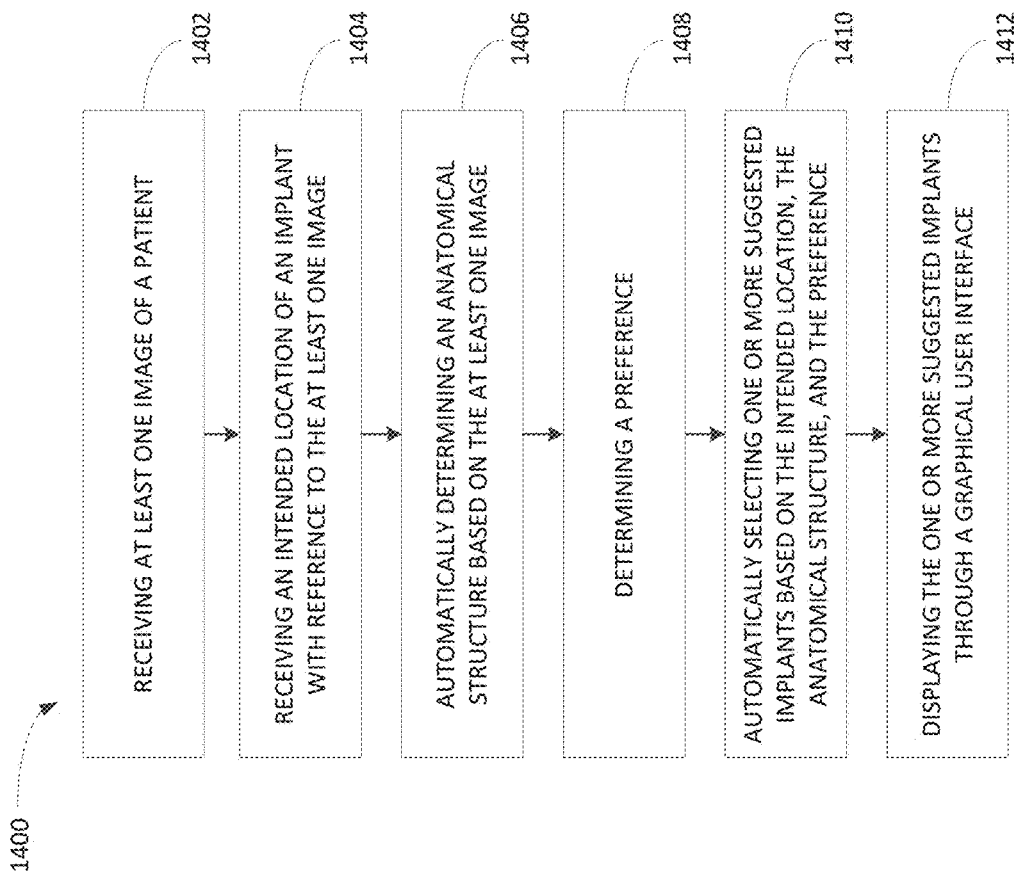
FIG. 14 is a flowchart of a method of automatically selecting an implant for a patient planning to undergo a procedure involving placement of the implant according to some embodiments.

For example, FIG. 14 illustrates a method 1400 performed by the server 102 (i.e., the electronic processor 104 executing instructions, such as the learning engine 110) for automatically selecting an implant for a patient planning to undergo a procedure involving placement of the implant according to some embodiments. As illustrated in FIG. 14, the method 1400 includes receiving, with the learning engine 110, at least one image of the patient from at least one data source 112 over an interface (e.g., the input/output interface 108) (at block 1402). For example, a physician may order images of a body part of the patient receiving an implant (e.g., using an electronic ordering system). Based on the order, the patient undergoes an imaging study where medical images are acquired (e.g., radiographic images). When the imaging study is complete, the captured images may be automatically sent to the learning engine 110 for processing (e.g., when the images are stored, such as in a RIS).

As illustrated in FIG. 14, the method 1400 also includes receiving, with the learning engine 110, an intended location of the implant with reference to the at least one image (at block 1404). In some embodiments, the intended location includes at least one anatomical structure or landmark, which may be manually specified by a user (e.g., through one or more peripheral devices) or automatically identified by the learning engine 110 as described above. When the learning engine 110 automatically identifies the landmark, the learning engine 110 may display the landmark to a user for approval or modification (e.g., through one or more peripheral devices). As described above, the learning engine 110 may use user modifications to an automatically-identified landmark as feedback to improve future landmark identification.

As illustrated in FIG. 14, the method 1400 also includes automatically determining, with the learning engine 110, an anatomical structure based on the at least one image (at block 1406). For example, as described above with respect to FIG. 5, the learning engine 110 may be configured to generate a diagnosis that includes an identification of an anatomical structure represented in an image. The method 1400 also includes determining, with the learning engine 110, a preference (at block 1408). The preference may include a preference of a physician performing the procedure, a preference for a particular manufacturer of implants or a particular supplier of implants, a preference for the procedure, an available implant, an available supplier or an available manufacturer, a preference of an organization, a preference of the patient, or a combination thereof. In some embodiments, as described above, preferences are configurable (e.g., by a user through a graphical user interface).

The learning engine 110 then automatically selects one or more suggested implants based on the intended location, the anatomical structure, and the preference (at block 1410). The learning engine 110 may display the one or more suggested implants through a graphical user interface (at block 1412).

In some embodiments, the learning engine 110 may also be configured to automatically add a suggested implant to the image. For example, the learning engine 110 may be configured to generate a modified image that includes the anatomical structure and one of the suggested implants where the learning engine 110 automatically configures (e.g., adjusts a shape and size) and positions the implant based on the intended location and is positioned based on the anatomical structure and the intended location.

The learning engine 110 may display the modified image to a user, such as within a graphical user interface. In some embodiments, a user may adjust the selection, configuration, position, or a combination thereof of the implant included in the modified image (e.g., through one or more peripheral devices). For example, the learning engine 110 may set a status of the modified image to "preliminary plan," and a physician (e.g., a surgeon) or an implant manufacturer or representative may access the "preliminary plan" (e.g., by logging into a storage location for "preliminary plans" or by automatically receiving the "preliminary plan," such as within an e-mail message or other type of electronic notification) to review the preliminary plan and make any desired adjustments. When no adjustments are needed or after any desired adjustments are made, the "preliminary plan" is approved. When a "preliminary plan" is approved, the learning engine 110 changes the status to "final" or "approved," and, in some embodiments, the learning engine 110 automatically sends the approved implant details to a manufacturer for implant manufacturing (e.g., customization if necessary) and manufacturing or acquisition of associated implant guides. Accordingly, the learning engine 110 may be used in orthopedic medicine to reduce turnaround time for receiving implants and human errors associated with such implant orders.

When adjustments are made to the "preliminary plan," the learning engine 110 may update any models used to select the implant or to determine the configuration and position of the implant. For example, in some embodiments, the learning engine 110 may develop a model based on training information as described above. The training information may include a plurality of images associated with implants, and the learning engine 110 may perform machine learning to detect patterns between particular implants and particular anatomical structures or other implant conditions (e.g., automatically learn how to identify anatomical landmarks and place implants based on example images of anatomical landmarks and associated implants positioned manually or automatically). Accordingly, the learning engine 110 may develop a model that can automatically select suggested implants as described above. In some embodiments, the learning engine 110 may also develop models for determining an intended location, determining an anatomical structure, determining a preference, or a combination thereof. Also, in some embodiments, the learning engine 110 may update these models based on post-procedure data (e.g., images, laboratory reports, a patient questionnaire answers, or a follow-up appointment) associated with at least one of the one or more suggested implants. Also, in some embodiments, the learning engine 110 may performance analytics or generate analytics or statistics associated with particular implants or implant conditions, such as a usage rate of an implant, a success rate of an implant, most commonly-used implants, implants associated with the fewest patient complaints, most properly-placed implants, an implant most commonly used for a particular type of patient, and the like.

Similarly, the learning engine 110 may be used to track clinical outcomes. Clinics, such as cancer centers often need to report on clinical outcomes. However, it is often difficult to map pathology reports to image diagnoses. For example, a good pathology result may rely on an accurate biopsy. However, biopsy accuracy may be limited by image quality and equipment used to perform the biopsy procedure. Accordingly, the learning engine 110 may be configured to automatically track clinical outcomes, which saves costs and may address accreditation needs. For example, FIG. 15 illustrates a method 1500 performed by the server 102 (i.e., the electronic processor 104 executing instructions, such as the learning engine 110) for mapping one or more biopsy locations to pathology results according to some embodiments.

Figure 15:
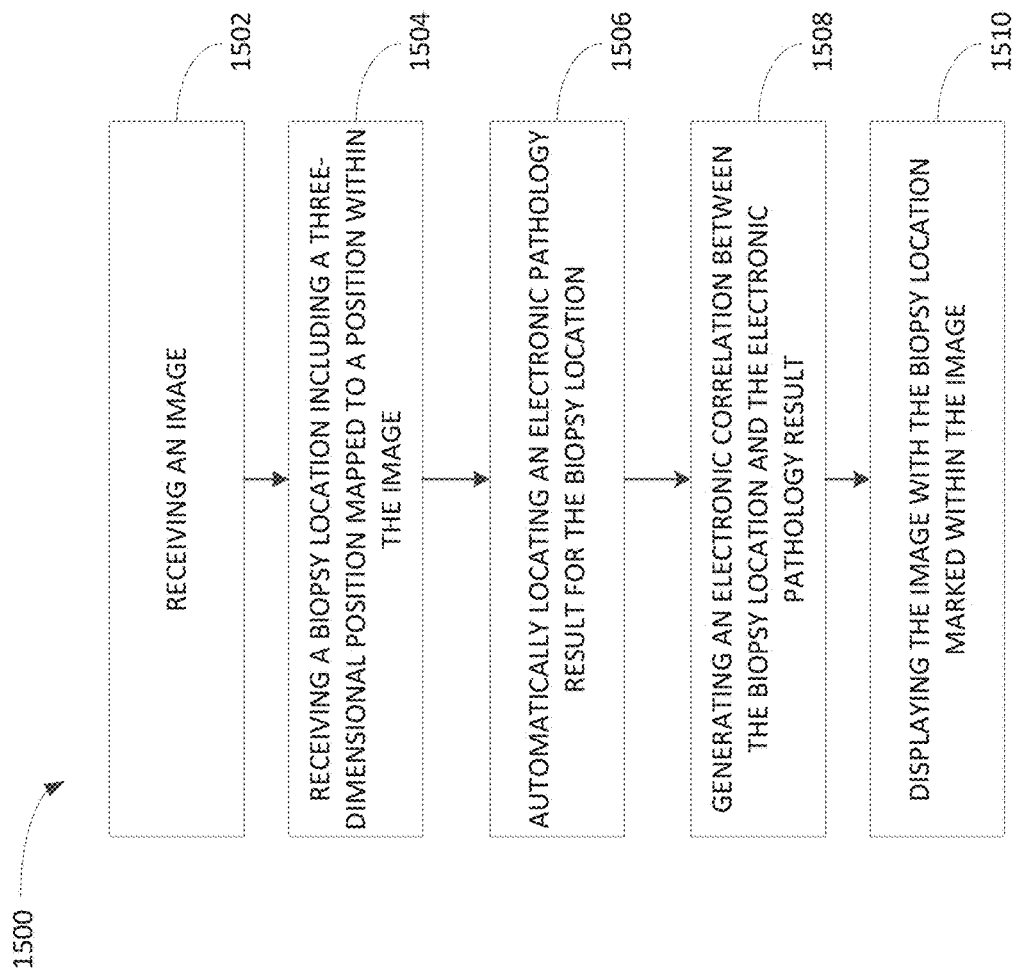
FIG. 15 is a flowchart of a method of mapping pathology results to clinical images according to some embodiments.

As illustrated in FIG. 15, the method 1500 includes receiving, with the learning engine 110, an image from at least one data source 115 over an interface (e.g., the input/output interface 108) (at block 1502). The method 1500 also includes receiving, with the learning engine 110, a biopsy location (at block 1504). The biopsy location includes a three-dimensional position mapped to a position within the image. In some embodiments, the learning engine 110 may automatically map a biopsy location to a position with the image based on medical information associated with the patient (such as additional images, patient information, and procedure information). For example, as part of a diagnosis associated with the image, a lesion or other area of interest may be graphically marked on the image, and the learning engine 110 may use this graphical reporting as described above to identify biopsy locations that may be specified for particular lesions or particular segments of a lesion (e.g., top, right corner of the lesion). Similarly, in some embodiments, the learning engine 110 develops a model as described above that map biopsy locations to particular locations within an associated image using training information that includes images included marked biopsy locations (e.g., manually marked locations).

As illustrated in FIG. 15, the learning engine 110 automatically locates an electronic pathology result for the biopsy location within the at least one pathology result source over the interface (at block 1506). The pathology result source may include an EMR or a MS. In some embodiments, the learning engine 110 uses a model (e.g., developed using machine learning) to locate the electronic pathology result. The model may extract pathology location information from one or more pathology reports and map each extracted pathology location to an associated image and, optionally, a location within the associated image. Similarly, in some embodiments, the learning engine 110 locates the electronic pathology result by deducting semantics from text included in a pathology report or searching for a field within a structured pathology report.

Figure 16:
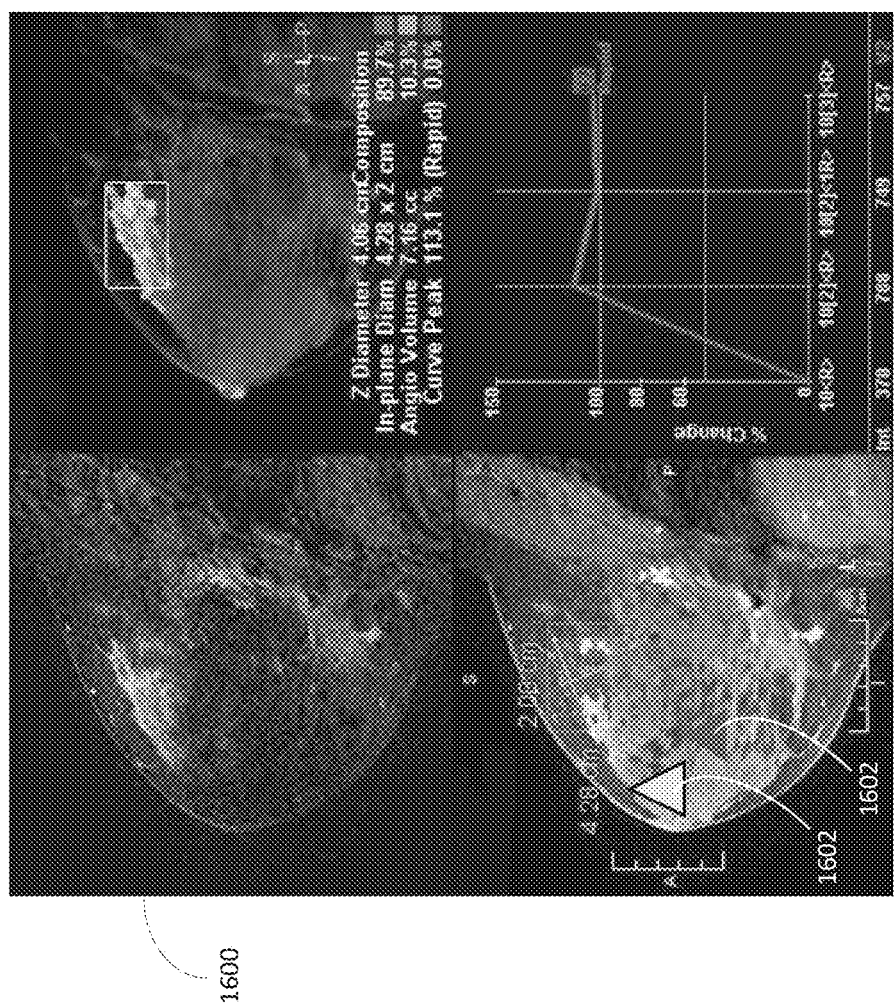
FIG. 16 illustrates an image including a plurality of marked biopsy locations according to some embodiments.
Figure 17:
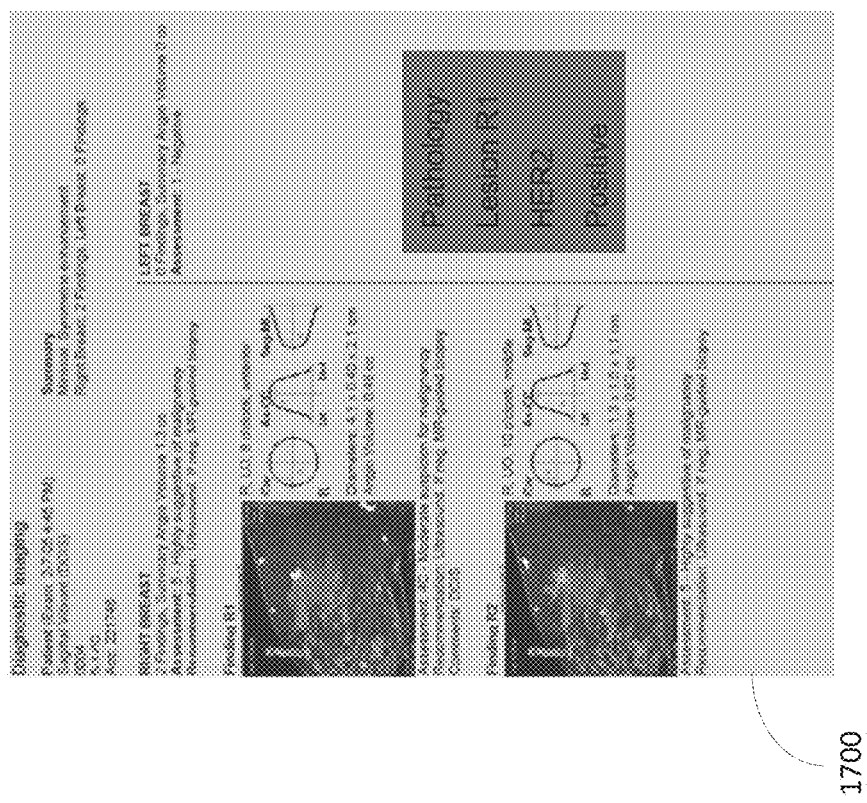
FIG. 17 illustrates a pathology report according to some embodiments.

The learning engine 110 also generates an electronic correlation between the biopsy location and the electronic pathology result (at block 1508). For example, in some embodiments, the learning engine 110 generates the electronic correlation by generating a table or other data structure that maps the biopsy location to the electronic pathology result. As illustrated in FIG. 15, the learning engine 110 also displays the image with the biopsy location marked within the image (at block 1510). For example, FIG. 16 illustrates an image 1600 with two marked biopsy locations 1602. As illustrated in FIG. 16, the image 1600 provides a user, such as a radiologist with an image (e.g., a three-dimensional image) of an organ with associated biopsied locations. In some embodiments, when a user selects the marked biopsy location 1602, the learning engine 110 automatically displays the corresponding electronic pathology result based on the electronic correlation. In some embodiments, the learning engine 110 displays the electronic pathology result within the associated pathology report (see, e.g., the example pathology report 1700 illustrated in FIG. 17). Also, in some embodiments, the learning engine 110 displays other pathology reports with the associated pathology report, such as past pathology reports, future pathology reports, or a combination thereof, to provide a user with a timeline of pathology results. In some embodiments, a user may enable or disable the marked biopsy locations 1602, such as using configurable preferences associated with the user. Also, in some embodiments, a user can specify preferences for characteristics of the marked biopsy locations 1602 (e.g., size, shape, color, orientation, etc.).

By correlating images and pathology reports, the learning engine 110 can perform a comparison between an original diagnosis associated with an image (i.e., prior to the pathology results) and the resulting pathology result. As described above, the learning engine 110 may use these comparisons to identify common errors or biases of diagnosing physicians. Similarly, the learning engine 110 may use these comparisons to update models used to automatically generate diagnoses.

Figure 18:
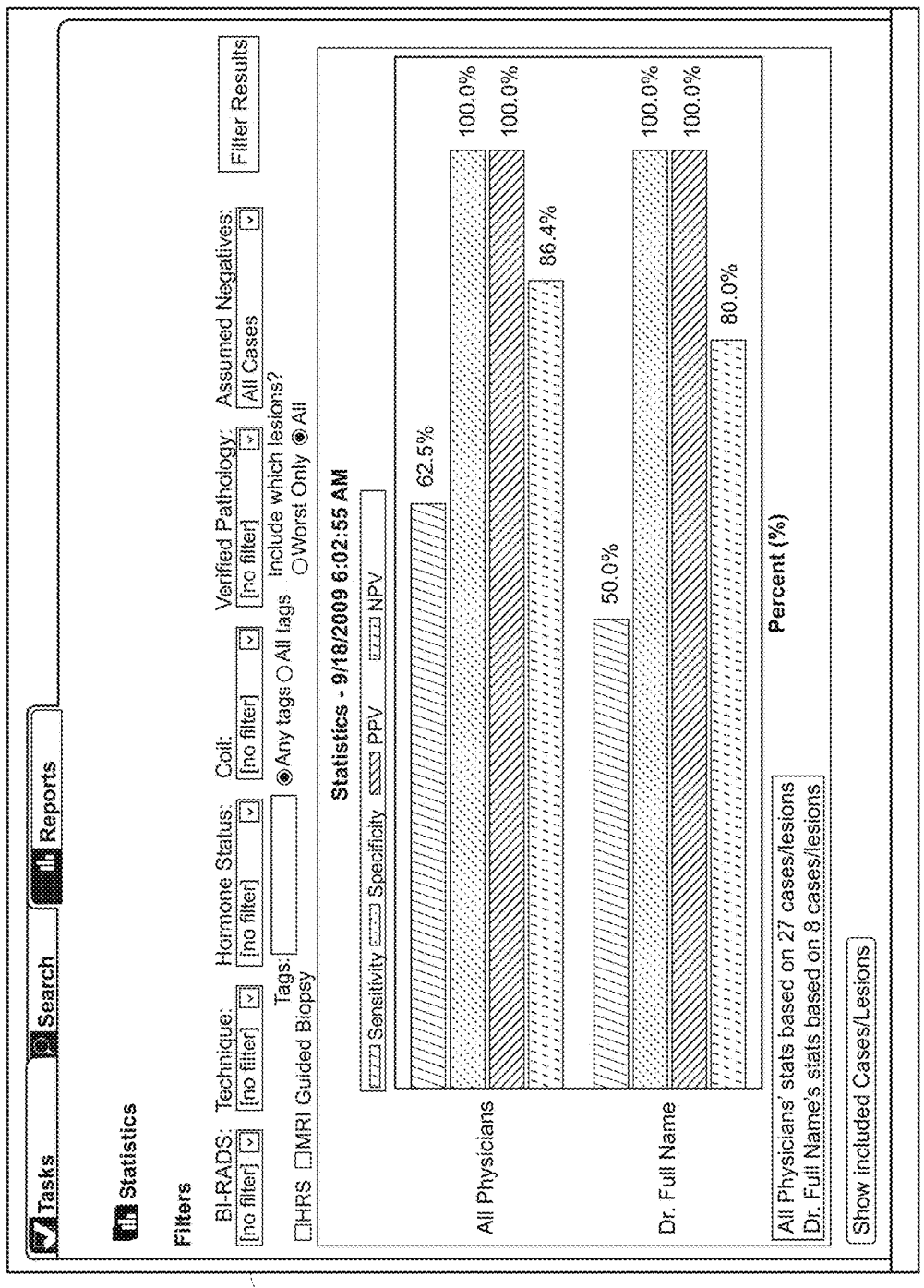
FIGS. 18 and 19 illustrate graphical user interfaces displaying statistics of clinical outcomes according to some embodiments.
Figure 19:
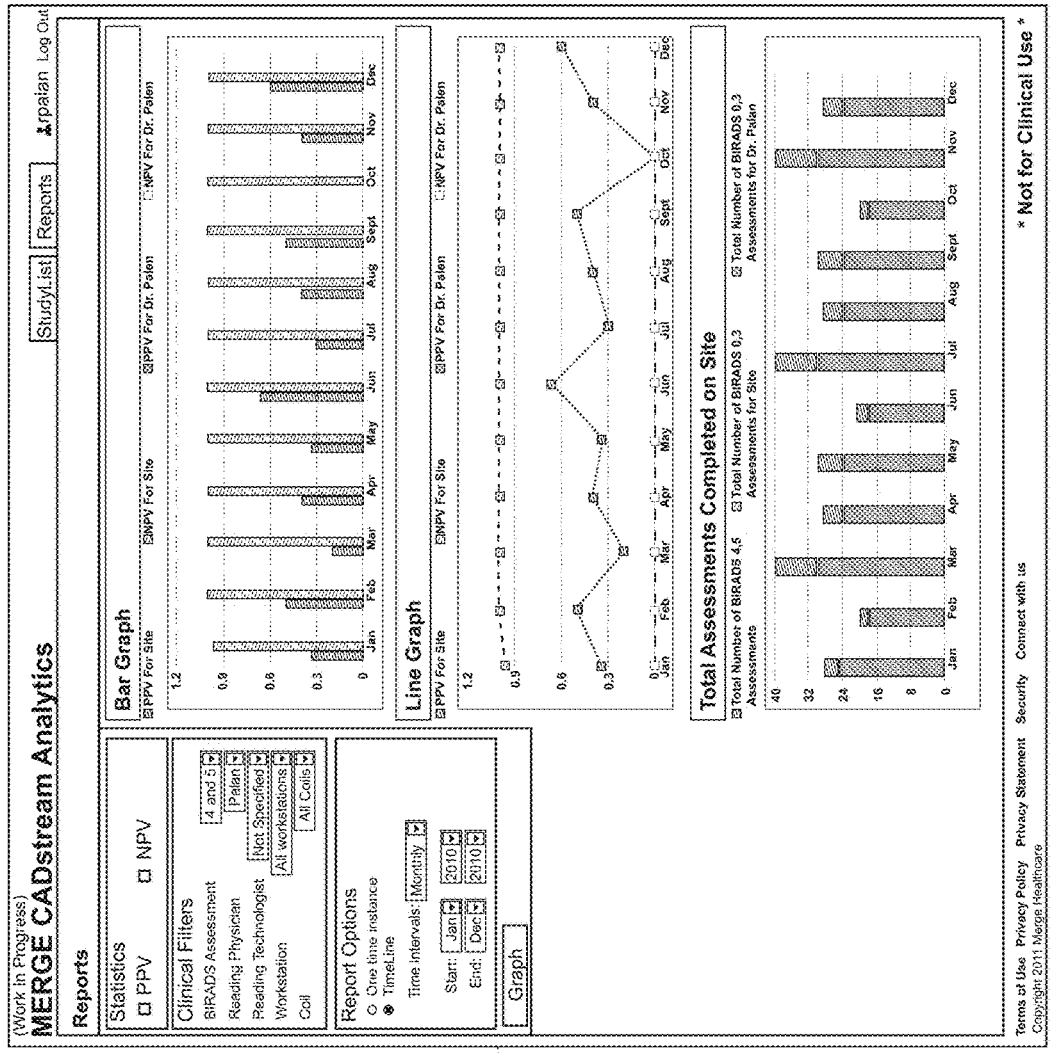

The learning engine 110 may also generate statistics and scores based on these comparisons, such as a percentage of diagnoses consistent with corresponding pathology results. For example, FIGS. 18 and 19 illustrate statistics that may be generated and displayed within graphical user interfaces 1800 and 1900 in various formats (e.g., line graphs, bar graphs, and the like). The statistics and scores may be used to facilitate internal quality assurance, such as by reviewing diagnosis and biopsy cases that are discordant and allowing a review of biopsy locations. Similarly, the statistics and scores may include a total number of cases interpreted and the statistical results of such cases to provide a quick snap-shot of the status of a clinical program. Also, in some embodiments, the learning engine 110 may generate a table that compares biopsy locations within images to corresponding electronic pathology results. For example, FIG. 20 illustrates a graphical user interface 2000 that includes a table 2002 listing image studies and associated pathology results.

As described above, the learning engine 110 may be configured to mark biopsy locations 1602 within an image, wherein the locations are linked to the corresponding pathology results. Conversely, in some embodiments, a pathology report is interactive, such that a user can view pathology locations within an image from the pathology report. For example, FIG. 21 illustrates a method 2100 performed by the server 102 (i.e., the electronic processor 104 executing instructions, such as the learning engine 110) for mapping pathology results to clinical images according to some embodiments.

Similar to the method 1500, the method 2100 includes receiving, with the learning engine 110, an image from at least one data source 112 over an interface (e.g., the input/output interface 108) (at block 2102), receiving, with the learning engine 110, a biopsy location includes a three-dimensional position mapped to a position within the image (at block 2104), automatically locating, with the learning engine 110, an electronic pathology result for the biopsy location within the at least one pathology result source over an interface (at block 2106), and generating, with the learning engine 110, an electronic correlation between the biopsy location and the electronic pathology result (at block 2108).

Figure 21:
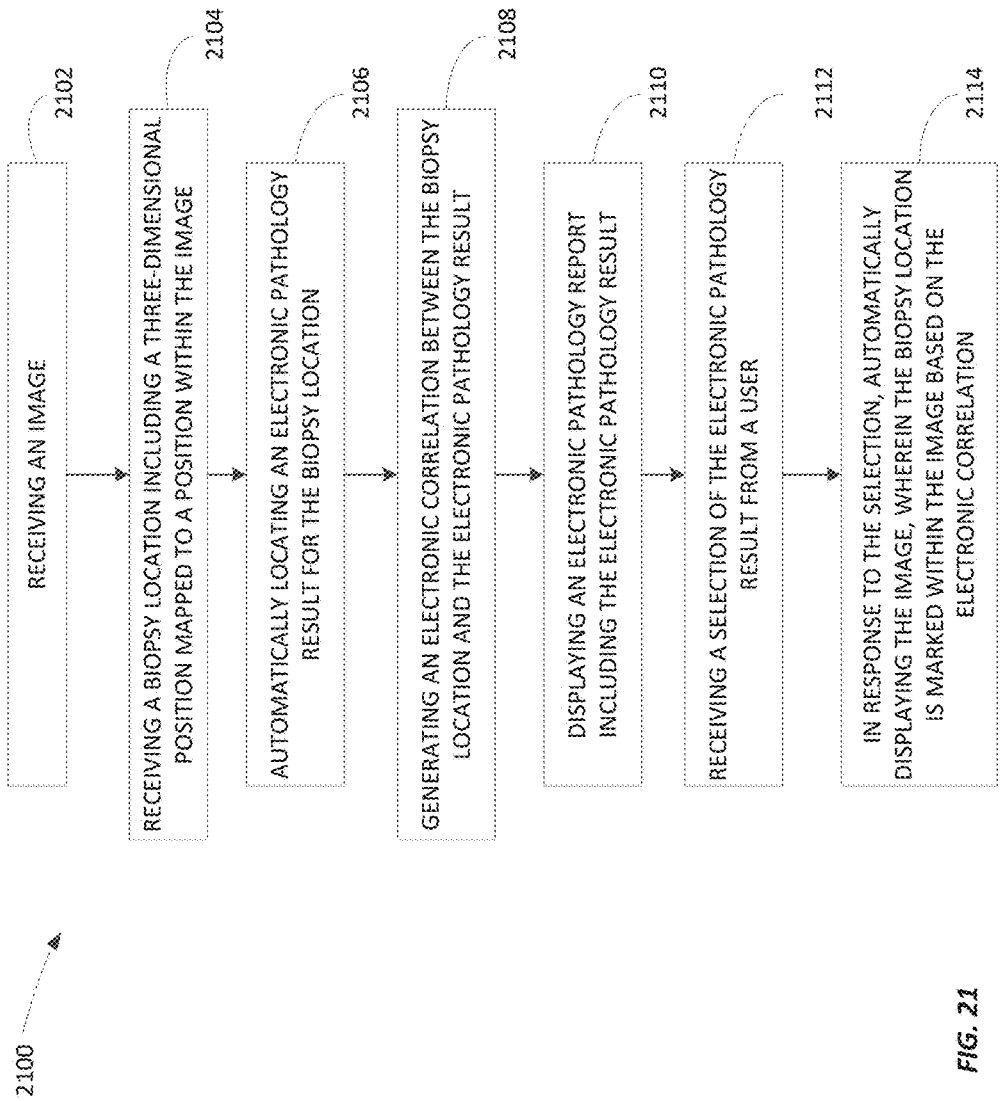
FIG. 21 is a flowchart of a method of mapping one or more biopsy locations to pathology results according to some embodiments.

As illustrated in FIG. 21, the learning engine 110 displays an electronic pathology report including the electronic pathology result (at block 2110), receives a selection of the electronic pathology result from a user (at block 2112), and, in response to the selection, automatically, displays the image, wherein the biopsy location is marked within the image based on the electronic correlation (at block 2114). Accordingly, while viewing a pathology report, a user may be able to select a particular pathology result (e.g., the result itself or an associated link or icon) to review the corresponding biopsy location within an image. In some embodiments, the learning engine 110 performs both of the methods 1500 and 2100 to allow a user to toggle between and the electronic pathology result and the associated marked biopsy locations within the associated image to navigate through biopsied locations.

Thus, the learning engine 110 may be configured to track and link pathology results to exact biopsy locations within an image. This tracking helps clinicians record, visualize, and locate pathologies obtained using biopsy devices within an image. Accordingly, this tracking helps diagnosis, treat, and follow-up on disease progression through a correlation between laboratory pathology results and medical imaging of the same patient.

Thus, embodiments described herein provide methods and systems for developing image analytics using machine learning for the healthcare industry. The methods described herein are described as being performed by the server 102 and, in particular, by the learning 110 as executed by the electronic processor 104. However, in some embodiments, one or more of the methods, or portions thereof, may be performed by software executed by the electronic processor 104 distinct from the learning engine 110, a device separate from the server 102, or a combination thereof. For example, in some embodiments, the learning engine 110 may develop the models as described above and a separate piece of software or a separate device may access the models to analyze images or perform other functions.

Various features and advantages of the invention are set forth in the following claims.

What is claimed is:

1. A system for automatically analyzing clinical images using rules and image analytics developed using graphical reporting associated with previously-analyzed clinical images, the system comprising:
    a server including an electronic processor and an interface for communicating with at least one data source, the electronic processor configured to
    receive training information from the at least one data source over the interface, the training information including a plurality of images and graphical reporting associated with each of the plurality of images, each graphical reporting including a graphical marker designating a portion of one of the plurality of images and diagnostic information associated with the portion of the one of the plurality of images, perform machine learning to develop a model using the training information,
receive an image for analysis,
determine a set of rules for the image, and
automatically process the image using the model and the set of rules to generate a diagnosis for the image.

2. The system of claim 1, wherein the electronic processor is configured to determine the set of rules based on a user viewing the image within an image review application.

3. The system of claim 1, wherein the electronic processor is configured to determine the set of rules based on a diagnosing physician performing a diagnosis of the image.

4. The system of claim 1, wherein the electronic processor is configured to determine the set of rules based on a physician ordering an image procedure during which the image was generated.

5. The system of claim 1, wherein the electronic processor is configured to determine the set of rules based on patient demographic information associated with the image.

6. The system of claim 1, wherein the electronic processor is configured to determine the set of rules based on an organization of diagnosing physicians associated with the image.

7. The system of claim 1, wherein the electronic processor is configured to determine the set of rules based on an organization of healthcare facilities associated with the image.

8. The system of claim 1, wherein the electronic processor is configured to determine the set of rules based on an organization associated with a workstation displaying the image.

9. The system of claim 1, wherein the electronic processor is configured to determine the set of rules based on a type of the image or a type of an imaging exam associated with the image.

10. The system of claim 1, wherein the electronic processor is configured to determine the set of rules based on a geographic location associated with the image.

11. The system of claim 10, wherein the geographic location includes a geographic location of a diagnosing physician associated with the image.

12. The system of claim 1, wherein the electronic processor is configured to determine the set of rules based on an imaging modality generating the image.

13. The system of claim 1, wherein the electronic processor is configured to determine the set of rules based on an image acquisition site associated with the image.

14. The system of claim 1, wherein the electronic processor is configured to determine the set of rules based on applicable epidemic information.

15. The system of claim 1, wherein the electronic processor is further configured to determine an anatomical structure represented in the image and wherein the electronic processor is configured to determine the set of rules based on the anatomical structure.

16. The system of claim 15, wherein the electronic processor is configured to determine the anatomical structure using the model.

17. The system of claim 1, wherein the electronic processor is further configured to generate a graphical user interface for displaying and modifying the set of rules.

* * * * *